United States Patent
Hackam et al.

(10) Patent No.: US 11,458,141 B2
(45) Date of Patent: Oct. 4, 2022

(54) ARYL HYDROCARBON RECEPTOR (AHR) AGONISTS FOR THE PREVENTION AND TREATMENT OF INFLAMMATORY DISORDERS

(71) Applicant: The Johns Hopkins University, Baltimore, MD (US)

(72) Inventors: David Joel Hackam, Baltimore, MD (US); Peng Lu, Lutherville Timonium, MD (US); Chhinder P. Sodhi, Columbia, MD (US); Jun O. Liu, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/617,247

(22) PCT Filed: May 25, 2018

(86) PCT No.: PCT/US2018/034636
§ 371 (c)(1),
(2) Date: Nov. 26, 2019

(87) PCT Pub. No.: WO2018/218143
PCT Pub. Date: Nov. 29, 2018

(65) Prior Publication Data
US 2020/0138821 A1 May 7, 2020

Related U.S. Application Data

(60) Provisional application No. 62/511,451, filed on May 26, 2017, provisional application No. 62/539,521, filed on Jul. 31, 2017.

(51) Int. Cl.
| | |
|---|---|
| *A61K 31/52* | (2006.01) |
| *A23L 33/10* | (2016.01) |
| *A23L 33/00* | (2016.01) |
| *A61P 29/00* | (2006.01) |
| *A61K 9/00* | (2006.01) |
| *A61K 31/192* | (2006.01) |
| *A61K 31/404* | (2006.01) |
| *A61K 31/4439* | (2006.01) |

(52) U.S. Cl.
CPC ............ *A61K 31/52* (2013.01); *A23L 33/10* (2016.08); *A23L 33/40* (2016.08); *A61K 9/0029* (2013.01); *A61K 9/0053* (2013.01); *A61K 31/192* (2013.01); *A61K 31/404* (2013.01); *A61K 31/4439* (2013.01); *A61P 29/00* (2018.01)

(58) Field of Classification Search
CPC .... A61K 31/52; A61K 31/192; A61K 31/404; A61K 31/4439
See application file for complete search history.

(56) References Cited

U.S. PATENT DOCUMENTS

| | | |
|---|---|---|
| 6,001,868 A | 12/1999 | Firestone et al. |
| 6,369,095 B1 | 4/2002 | Firestone et al. |
| 6,656,963 B2 | 12/2003 | Firestone et al. |

FOREIGN PATENT DOCUMENTS

| | | | |
|---|---|---|---|
| JP | 2015-145343 | 8/2015 | |
| WO | WO-2016189562 A1 * | 12/2016 | ......... A61K 31/4439 |

OTHER PUBLICATIONS

Bisquera et al. Impact of Necrotizing Enterocolitis on Length of Stay and Hospital Charges in Very Low Birth Weight Infants. Pediatrics., (2002), 109 (3), pp. 423-482.
Busbee et al. Use of Natural AhR Ligands as Potential Therapeutic Modalities Against Inflammatory Disorders. Nutr Rev., (2013), 71 (6), pp. 353-369.
Egan et al. Toll-like receptor 4-mediated lymphocyte influx induces neonatal necrotizing enterocolitis. J Clin Invest., (2016), 126 (2), pp. 495-508.
Esser et al. The aryl hydrocarbon receptor in barrier organ physiology, immunology, and toxicology. Pharmacological Reviews., (2015), 67 (2), pp. 259-279.
Ganapathy et al. Costs of Necrotizing Enterocolitis and Cost-Effectiveness of Exclusively Human Milk-Based Products in Feeding Extremely Premature Infants. Breastfeeding Medicine., (2012), 7 (1), pp. 29-42.
Gargaro et al. Aryl Hydrocarbon Receptor-Dependent Pathways in Immune Regulation. American Journal of Transplantation., (2016), 16 (8), pp. 2270-2276.
Good et al. The human milk oligosaccharide 2'-fucosyllactose attenuates the severity of experimental necrotising enterocolitis by enhancing mesenteric perfusion in the neonatal intestine. The British Journal of Nutrition., (2016), 116 (7), pp. 1175-1187.
Gribar et al. Reciprocal expression and signaling of TLR4 and TLR9 in the pathogenesis and treatment of necrotizing enterocolitis. J Immunol., (2009), 182 (1), pp. 636-646.
Hu et al. Induction of Cyp1a1 is a nonspecific biomarker of aryl hydrocarbon receptor activation: results of large scale screening of pharmaceuticals and toxicants in vivo and in vitro. Molecular Pharmacology., (2007), 71 (6), pp. 1475-1486.
Neu et al. Necrotizing enterocolitis. N Engl J Med., (2011), 364 (3), pp. 255-264.
Nino et al. Necrotizing enterocolitis: new insights into pathogenesis and mechanisms. Nature Reviews Gastroenterology & Hepatology., (2016), 13 (10), pp. 590-600.
Patel et al. Causes and timing of death in extremely premature infants from 2000 through 2011. N Engl J Med., (2015), 372 (4), pp. 331-340.
Reed et al. A Phase I Study of Indole-3-Carbinol in Women: Tolerability and Effects. Cancer Epidemiol Biomarkers Prev., (2005), 14 (8), pp. 1953-1960.
Shibuyama et al., Understanding and Avoiding Antiretroviral Adverse Events. Curr Pharm Des., (2006), 12 (9), pp. 1075-1090.

(Continued)

*Primary Examiner* — Kevin E Weddington
(74) *Attorney, Agent, or Firm* — Casimir Jones, S.C.

(57) ABSTRACT

Aryl hydrocarbon receptor (AHR) agonists and their use for treating, preventing, or reducing the risk of necrotizing enterocolitis in premature infants are disclosed.

9 Claims, 31 Drawing Sheets
(25 of 31 Drawing Sheet(s) Filed in Color)

(56) References Cited

OTHER PUBLICATIONS

Shivanna et al. Omeprazole attenuates pulmonary aryl hydrocarbon receptor activation and potentiates hyperoxia-induced developmental lung injury in newborn mice. Toxicological Sciences., (2015), 148 (1), pp. 276-287.

Shulhan et al. Current Knowledge of Necrotizing Enterocolitis in Preterm Infants and the Impact of Different Types of Enteral Nutrition Products. Adv Nutr., (2017), 8 (1), pp. 80-91.

Singh et al. Chemokine and cytokine levels in inflammatory bowel disease patients. Cytokine., (2016), J77, pp. 44-49.

Sodhi et al. Intestinal epithelial Toll-like receptor 4 regulates goblet cell development and is required for necrotizing enterocolitis in mice. Gastroenterology., (2012), 143 (3), pp. 708-718.e1-5.

Spencer et al. Pediatric Short-Bowel Syndrome: The Cost of Comprehensive Care. Am J Clin Nutr., (2008), 88 (6), pp. 1552-1159.

Stey et al. Outcomes and costs of surgical treatments of necrotizing enterocolitis. Pediatrics., (2015), 135 (5), pp. e1190-e1197.

Tarnow-Mordi Tarnow-Mordi et al. Probiotics Reduce All-Cause Mortality and Necrotizing Enterocolitis: It Is Time to Change Practice. Pediatrics., (2010), 125 (5), pp. 1068-1070.

Van Der Heiden et al. Food flavonoid aryl hydrocarbon receptor-mediated agonistic/antagonistic/synergic activities in human and rat reporter gene assays. Analytica chimica acta., (2009), 637, pp. 337-345.

Yoshinari et al. Omeprazole transactivates human CYP1A1 and CYP1A2 expression through the common regulatory region containing multiple xenobiotic-responsive elements. Biochemical Pharmacology., (2008), 76 (1), pp. 139-145.

International Search Report and Written Opinion for PCT/US2018/034636, dated Sep. 17, 2018, 13 pages.

\* cited by examiner

ARYL HYDROCARBON RECEPTOR (AHR) AGONISTS FOR THE PREVENTION AND TREATMENT OF INFLAMMATORY DISORDERS

CROSS-REFERENCE TO RELATED APPLICATIONS

This application is a § 371 U.S. National Entry Application of PCT/US2018/034636, filed May 25, 2018, which claims the benefit of U.S. Provisional Application No. 62/511,451, filed May 26, 2017, and U.S. Provisional Application No. 62/539,521, filed Jul. 31, 2017, the contents of which are incorporated herein by reference in their entirety.

FEDERAL FUNDING STATEMENT

This invention was made with government support under DK117186, awarded by the National Institutes of Health. The government has certain rights in the invention.

BACKGROUND

Necrotizing enterocolitis (NEC) is the leading cause of death from gastrointestinal disease in premature infants, afflicting newborns at a rate of 1 to 3 per 1000 births per year, Patel et al., 2015, with an average total treatment cost of $500,000 per patient in the United States in current charges. Stey et al., 2015. Importantly, the mechanisms leading to the development of NEC in premature infants, and the lessons learned from management of patients with NEC, may have broad implications to other neonatal inflammatory processes. Yet, despite several decades of experience in treating patients with NEC, the overall mortality and approach to treatment have remained largely unchanged since its initial descriptions several decades ago. Nino et al., 2016; Neu and Walker, 2011.

The main risk factors for the development of NEC are prematurity, bacterial colonization and administration of formula feeds, which in the setting of an abnormal microbiome lead to enhanced signaling via the lipopolysaccharide receptor toll like receptor 4 (TLR4), which is expressed at high levels on the premature as compared with the full term intestinal epithelium. Nino et al., 2016; Gribar et al., 2009. TLR4 activation leads to an influx of pro-inflammatory Th17 lymphocytes and reduction in anti-inflammatory Treg lymphocytes, Egan et al., 2016, which act on the lining of the intestine to cause mucosal injury, bacterial translocation and the development of systemic sepsis. Importantly, there is no specific treatment for NEC, and the overall survival for patients with this disease has not changed in the past 30 years.

SUMMARY

In some aspects, the presently disclosed subject matter provides a method for treating or preventing or reducing the risk of an inflammatory disorder associated with a reduced expression of an aryl hydrocarbon receptor (AhR) in a subject in need of treatment thereof, the method comprising administering to the subject one or more AhR agonists, or pharmaceutically acceptable salts thereof, to activate the AhR, thereby treating or preventing or reducing the risk of the inflammatory disorder.

In certain aspects, the inflammatory disorder is necrotizing enterocolitis. In yet more certain aspects, the subject is a premature infant.

In other aspects, the presently disclosed subject matter provides a method for preventing, reducing the risk of, or reducing the severity of an inflammatory disorder associated with a reduced expression of an aryl hydrocarbon receptor (AhR) in a subject in need of treatment thereof, the method comprising administering to a mother while pregnant with the subject one or more AhR agonists, or pharmaceutically acceptable salts thereof, to activate the AhR, thereby treating or preventing, reducing the risk of, or reducing the severity of the inflammatory disorder.

In certain aspects, the mother is at risk for delivering the subject prematurely.

In other aspects, the presently disclosed subject matter provides an infant nutritional formula comprising a therapeutically effective amount of one or more aryl hydrocarbon receptor (AhR) agonists, or pharmaceutically acceptable salts thereof.

In particular aspects, the infant nutritional formula is nutritionally complete.

In yet more particular aspects, the formula is adapted for enteral administration, either oral or gastric, to an infant.

The one or more AhR agonists of the presently disclosed subject matter can be selected from the group consisting of abacavir, abacavir sulfate, amlexanox, anagrelide hydrochloride, benzocaine (ethyl p-aminobenzoate), bromindione, catharanthine, dexlansoprazole, eseroline, febuxostat, helenien (xantofyl palmitate), hydralazine hydrochloride, indoprofen, ipratropium bromide, lansoprazole, menadione sodium bisulfate, nitazoxanide, omeprazole, phenazopyridine, phenazopyridine hydrochloride, primaquine, rabeprazole sodium, tenatoprazole, tranilast (sb 252218), and ziprasidone hydrochloride, indole-3-carbinol (I3C), A18, or derivatives and combinations thereof, or pharmaceutically acceptable salts thereof.

In certain aspects, the one or more AhR agonists is a compound of formula (I):

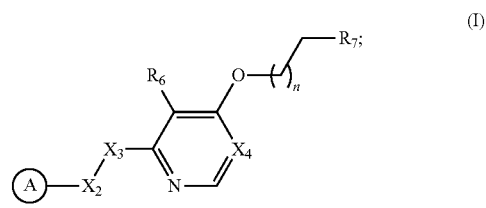

wherein:
n is an integer selected from the group consisting of 0, 1, and 2;
A is selected from the group consisting of

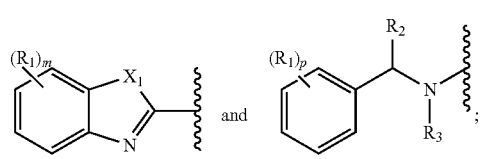

wherein:
m is an integer selected from the group consisting of 0, 1, 2, 3, and 4;
p is an integer selected from the group consisting of 0, 1, 2, 3, 4, and 5;

each $R_1$ is independently selected from the group consisting of H, $C_1$-$C_6$ alkyl, $C_1$-$C_6$ substituted alkyl, alkoxyl, halogen, and —$CF_3$;

$R_2$ and $R_3$ are each independently selected from the group consisting of H, $C_1$-$C_6$ alkyl, $C_1$-$C_6$ substituted alkyl, aryl, substituted aryl, heteroaryl, and benzyl;

$X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$X_2$ is selected from the group consisting of —S—, —S(=O)—, —S(=O)$_2$—, and —C(=O)—;

$X_3$ is selected from the group consisting of —$CH_2$— and —$NR_5$—, wherein $R_5$ is selected from the group consisting of H, $C_1$-$C_6$ alkyl, $C_1$-$C_6$ substituted alkyl, aryl, substituted aryl, heteroaryl, and benzyl;

$X_4$ is selected from the group consisting of —N— and —$CR_5$—, wherein $R_5$ is selected from the group consisting of H, $C_1$-$C_6$ alkyl, $C_1$-$C_6$ substituted alkyl, alkoxyl, halogen, and —$CF_3$;

$R_6$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$R_7$ is selected from the group consisting of H, $C_1$-$C_6$ alkyl, $C_1$-$C_6$ substituted alkyl, alkoxyl, halogen, —$CF_3$, aryl, substituted aryl, heteroaryl, and benzyl; or pharmaceutically acceptable salts thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1:
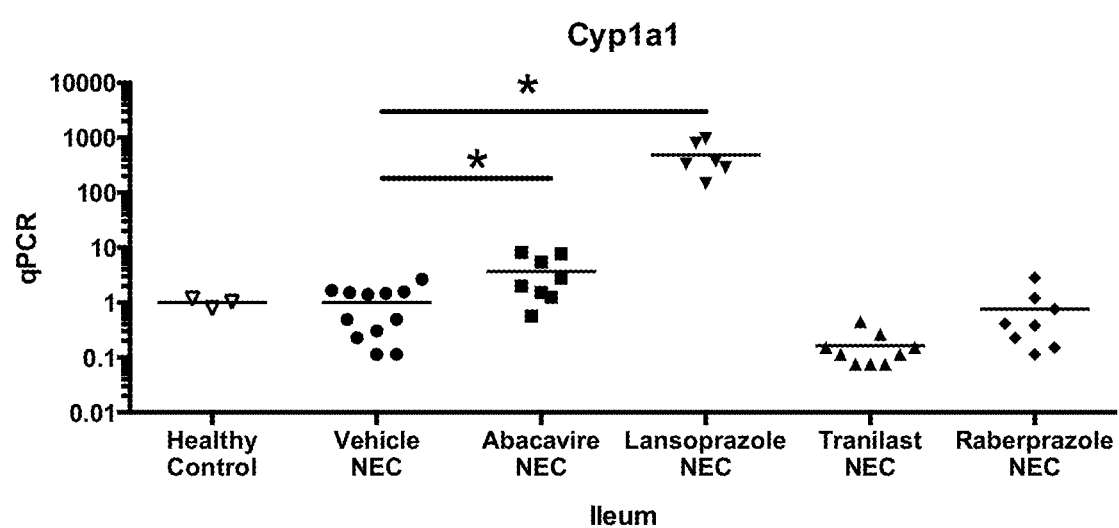
Figure 2:
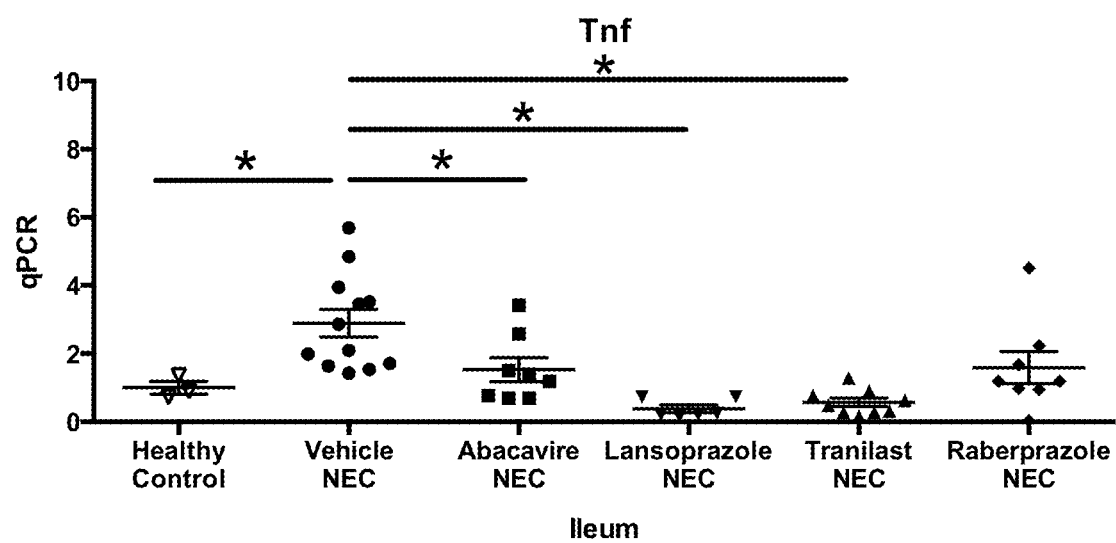
Figure 3:
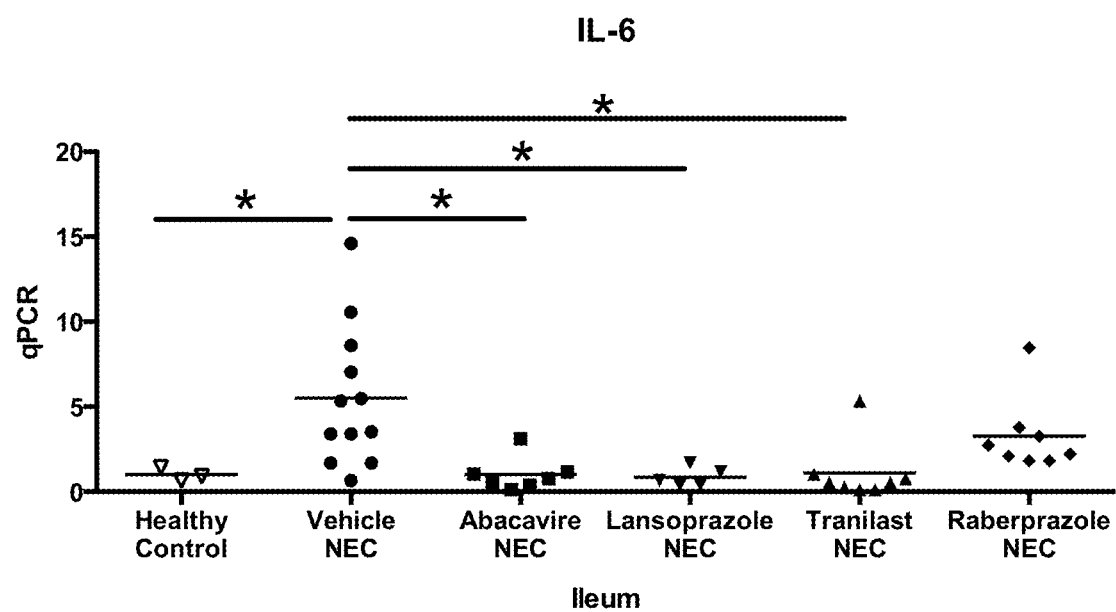
Figure 4:
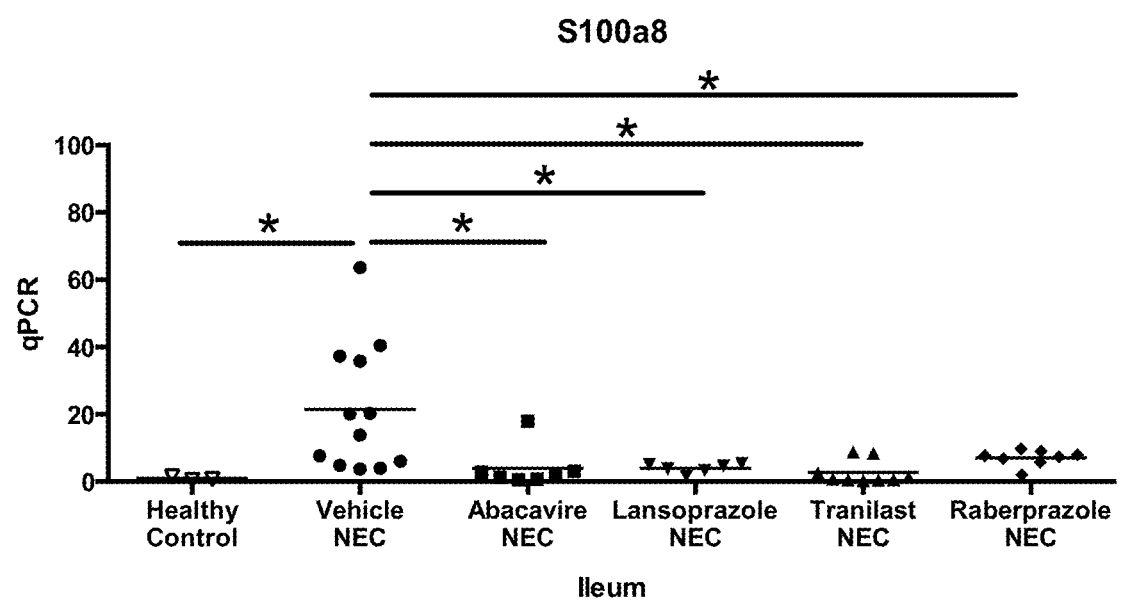
Figure 5:
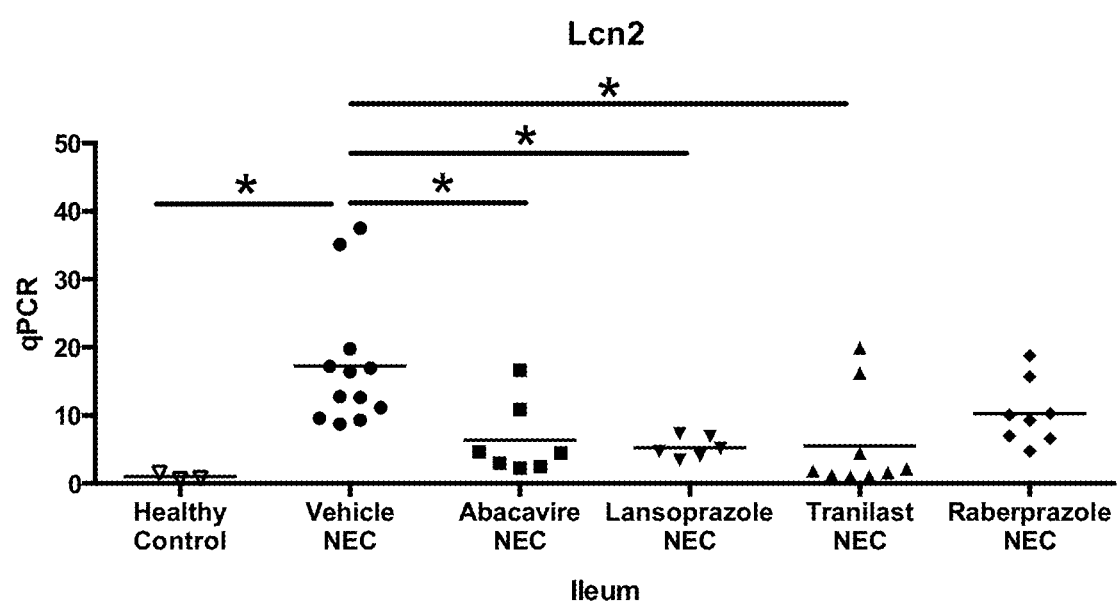
Figure 6:
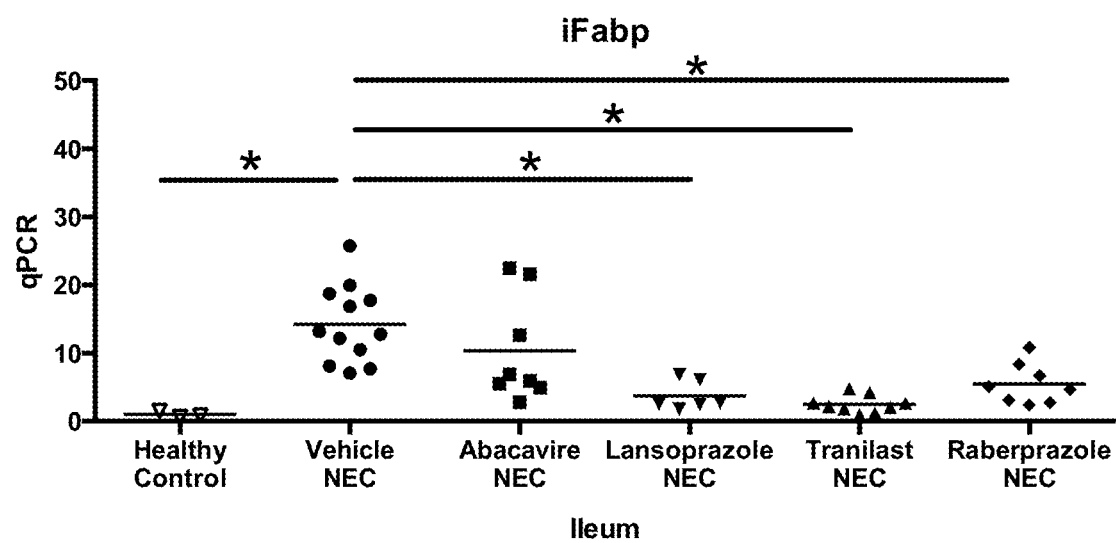
Figure 7:
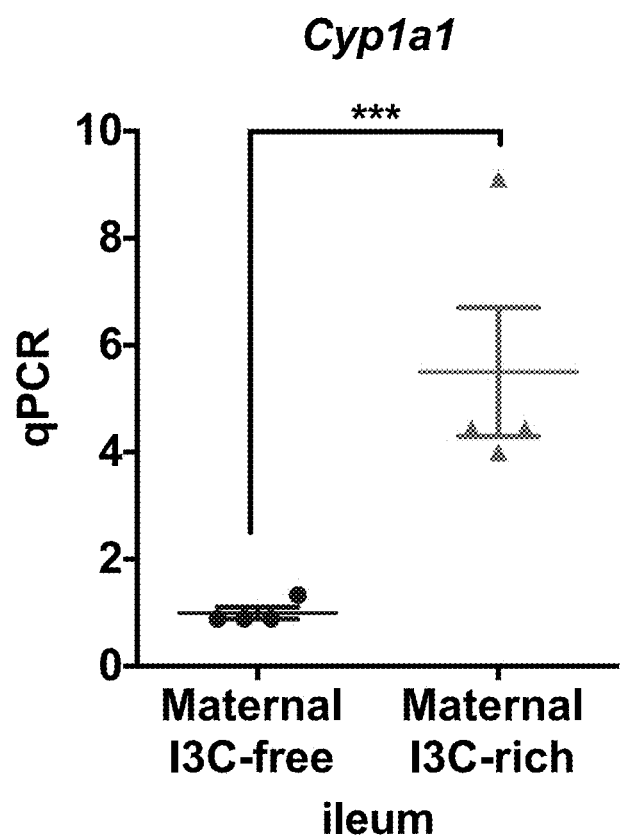
Figure 8:
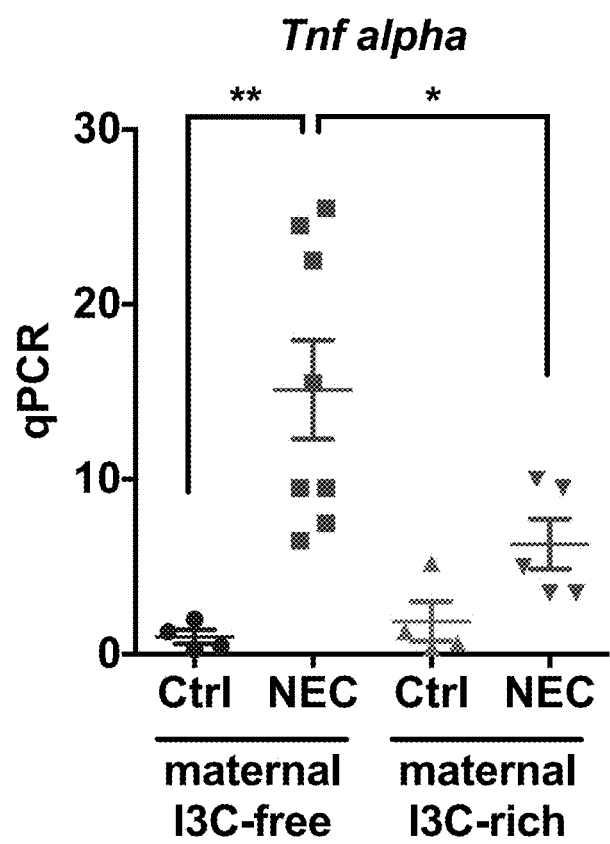
Figure 9:
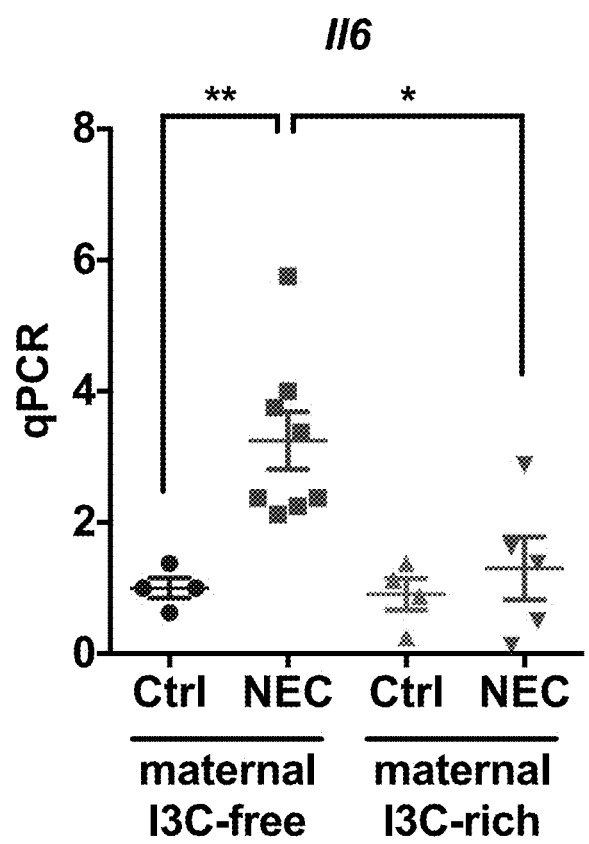
Figure 10A:
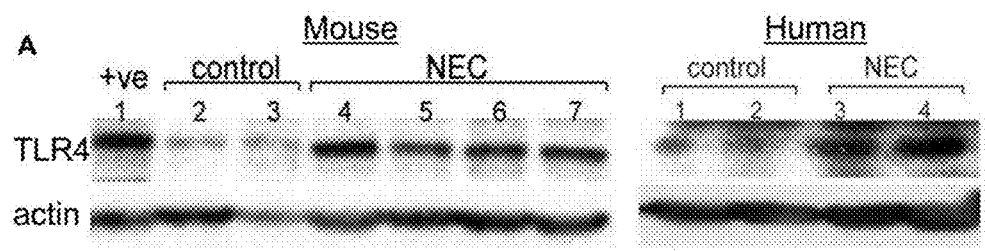
Figure 10B:
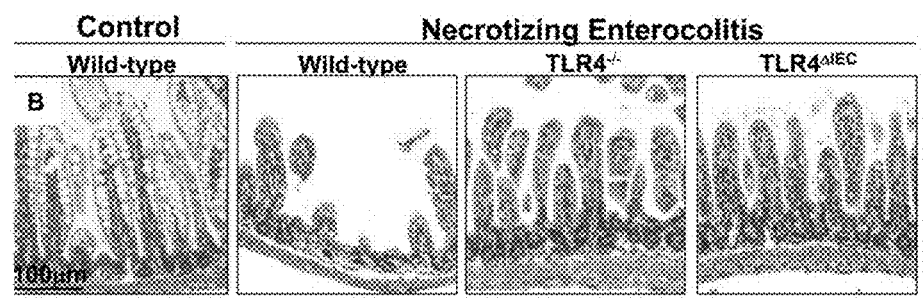
Figure 10C:
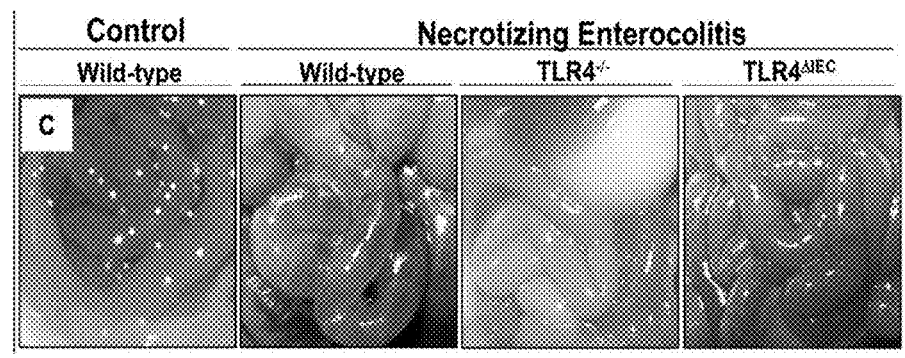
Figure 10D:
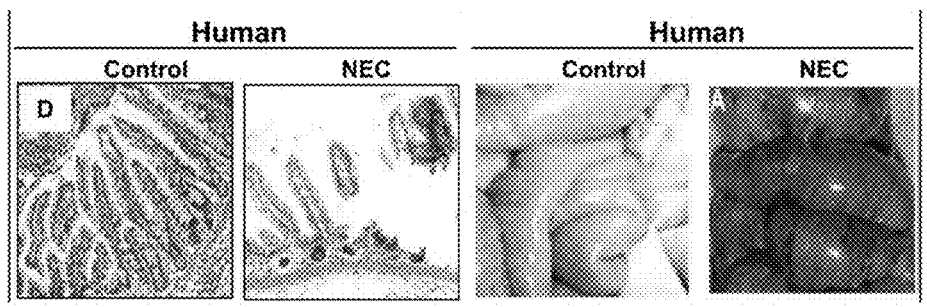
Figure 10E:
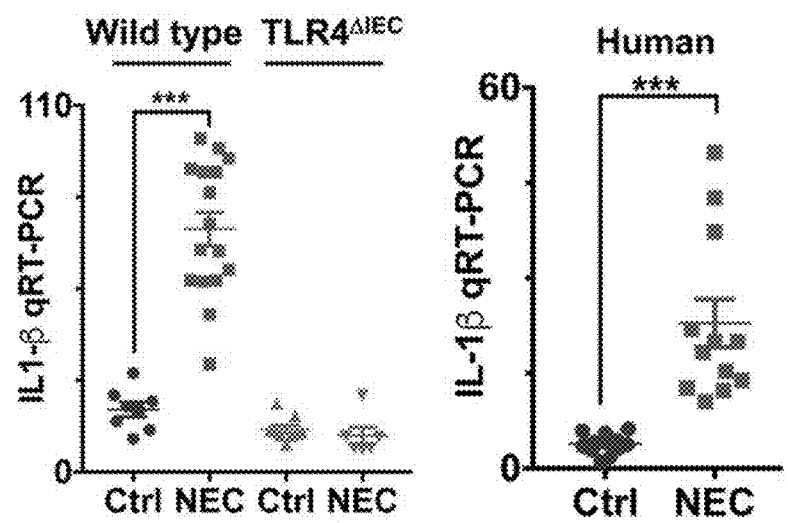
Figures 11A, 11B, 11C, 11D:
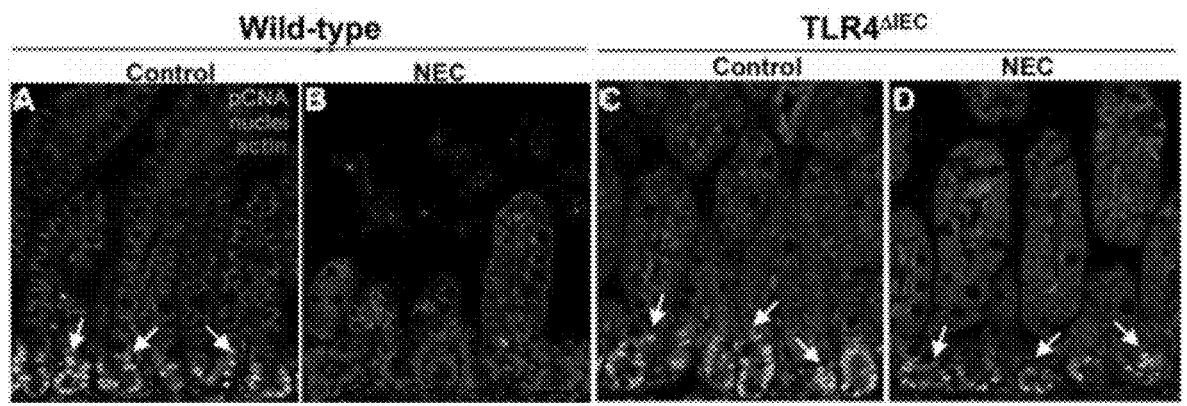
Figures 11E, 11F, 11G, 11H:
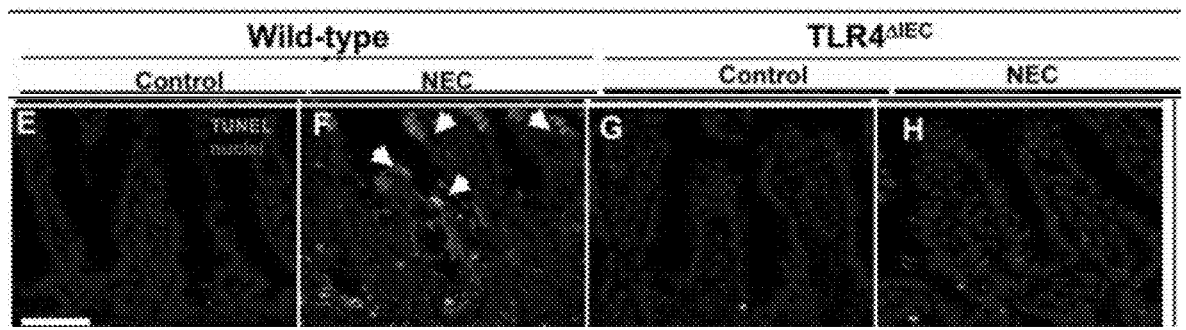
Figure 11I:
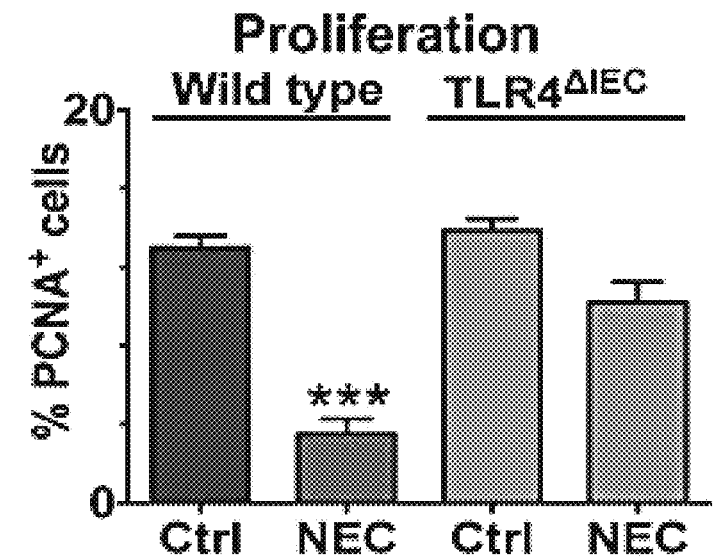
Figure 11J:
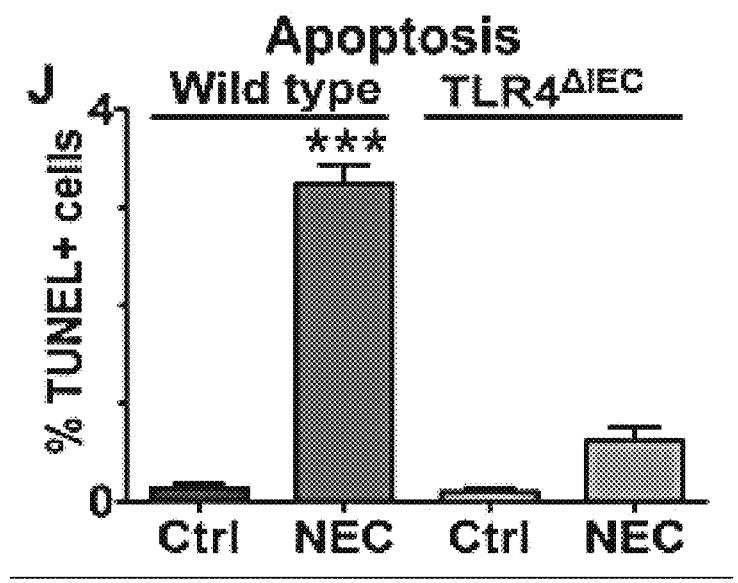
Figure 12:
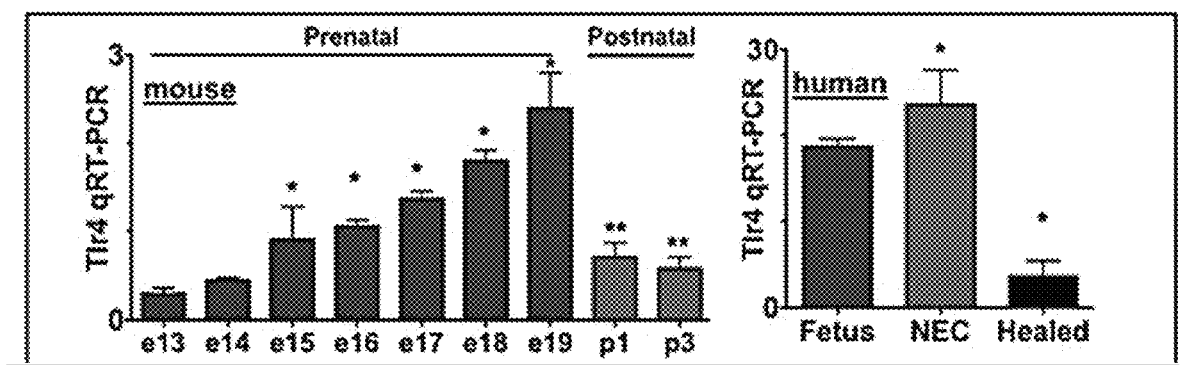
Figure 13A:
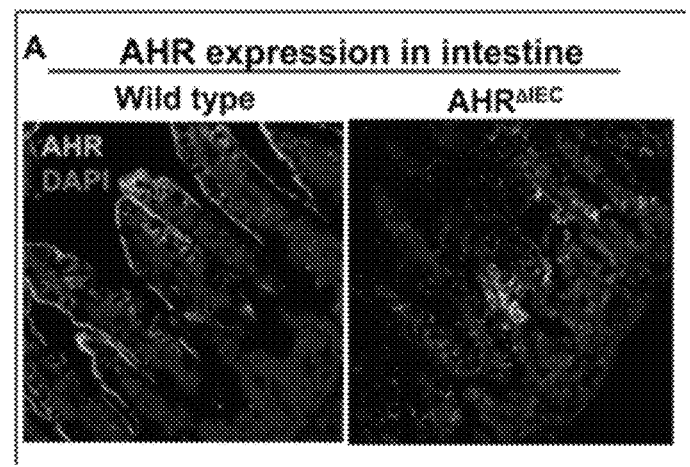
Figure 13B:
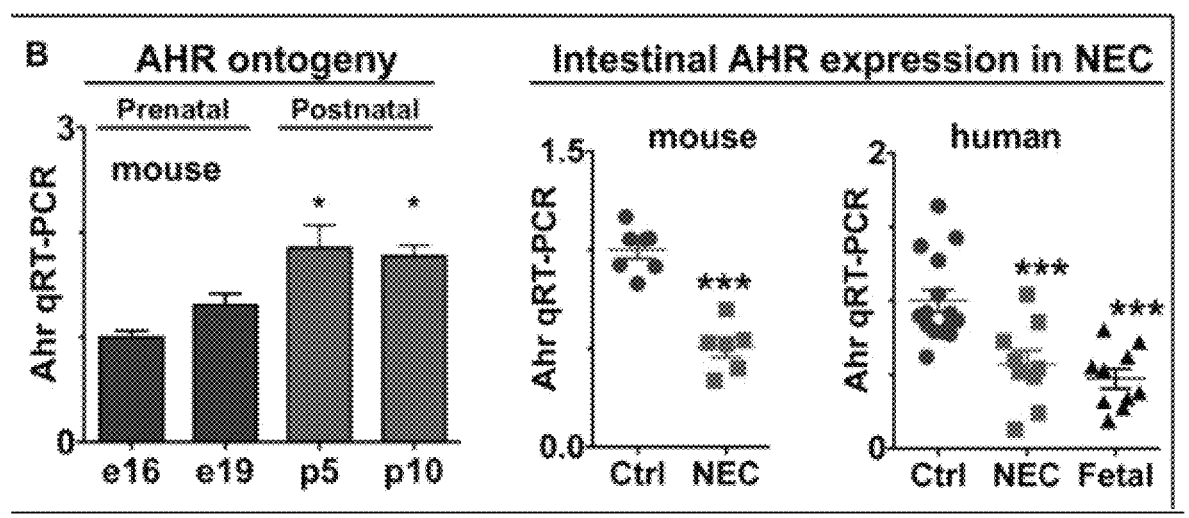
Figure 13C:
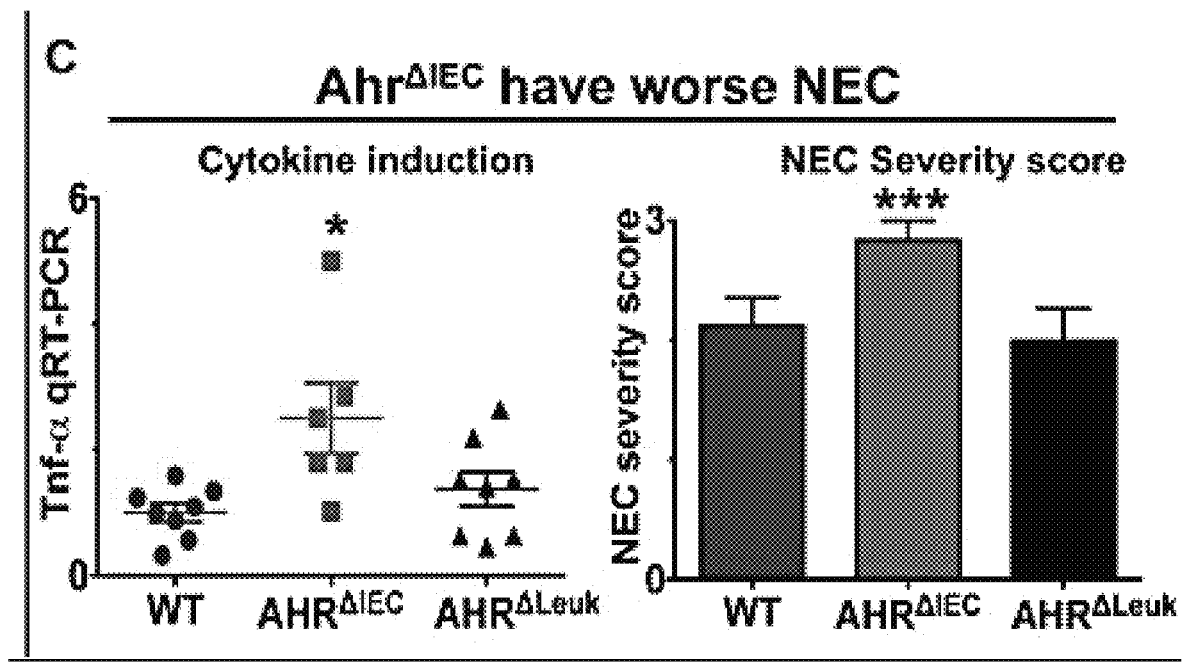
Figure 13D:
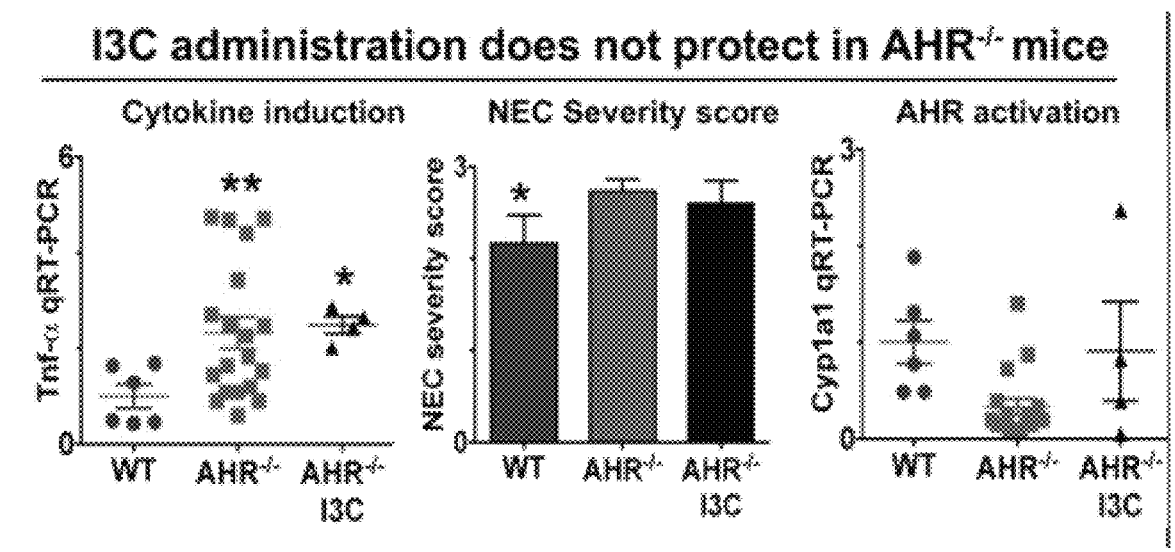
Figure 13E:
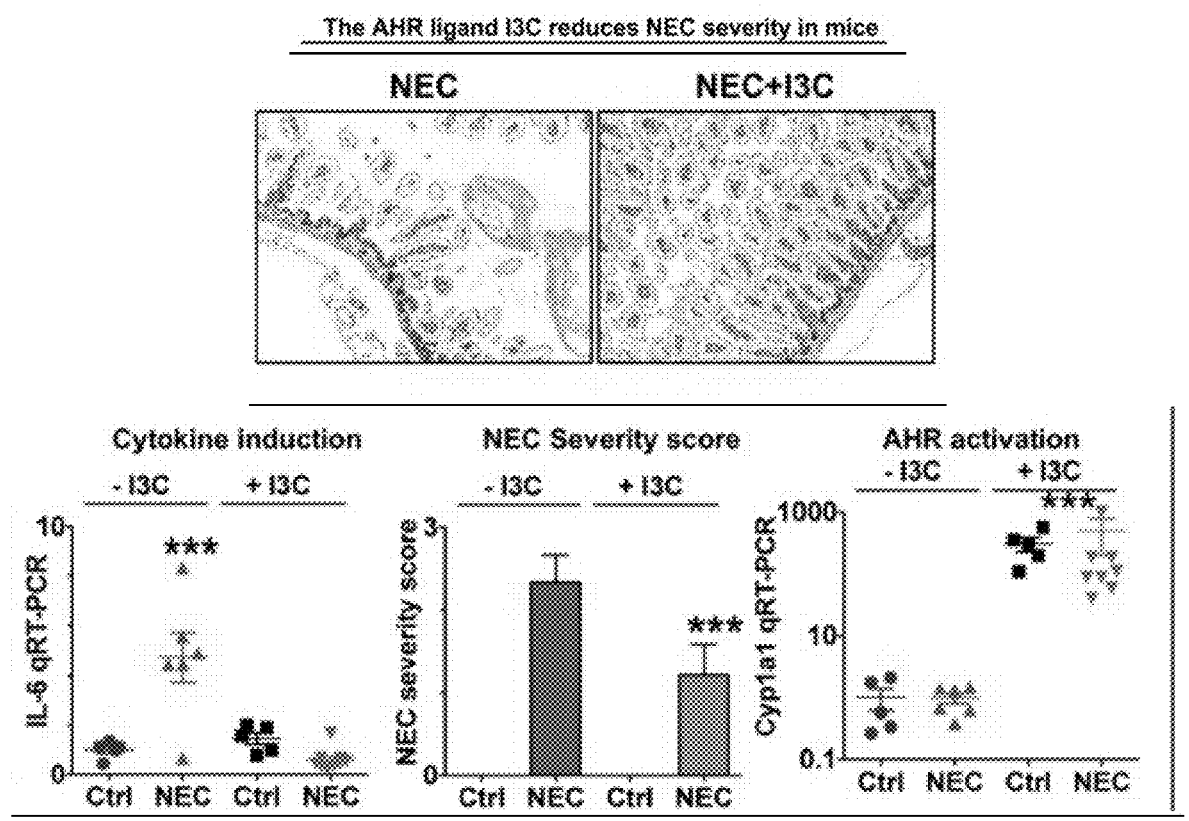
Figure 14A:
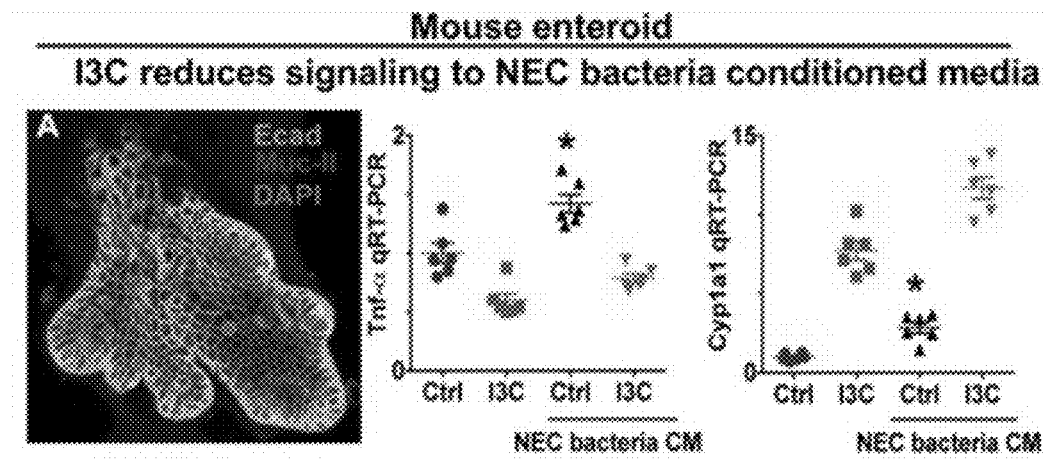
Figure 14B:
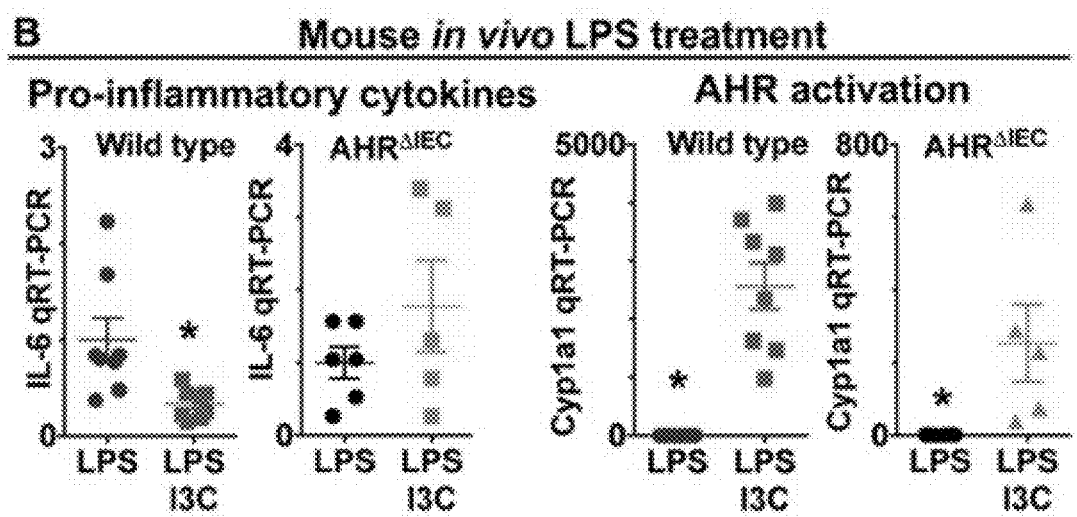
Figure 14C:
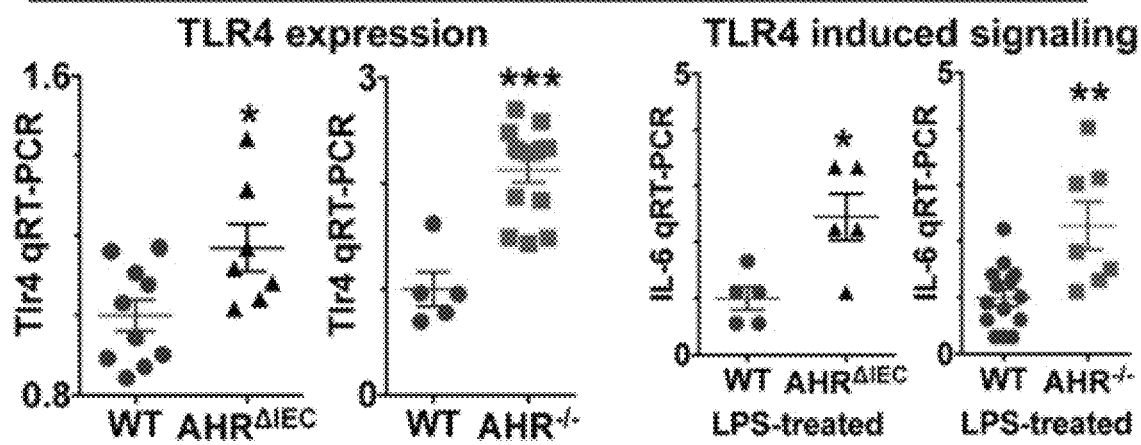
Figure 14D:
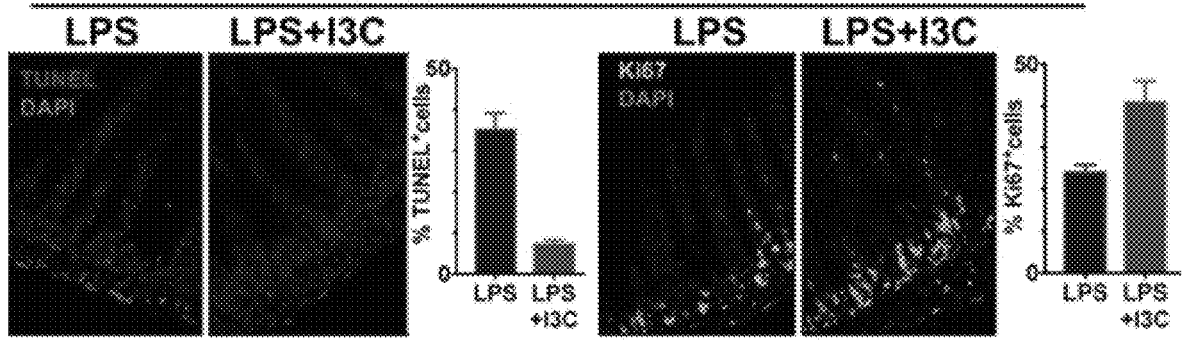
Figure 15A:
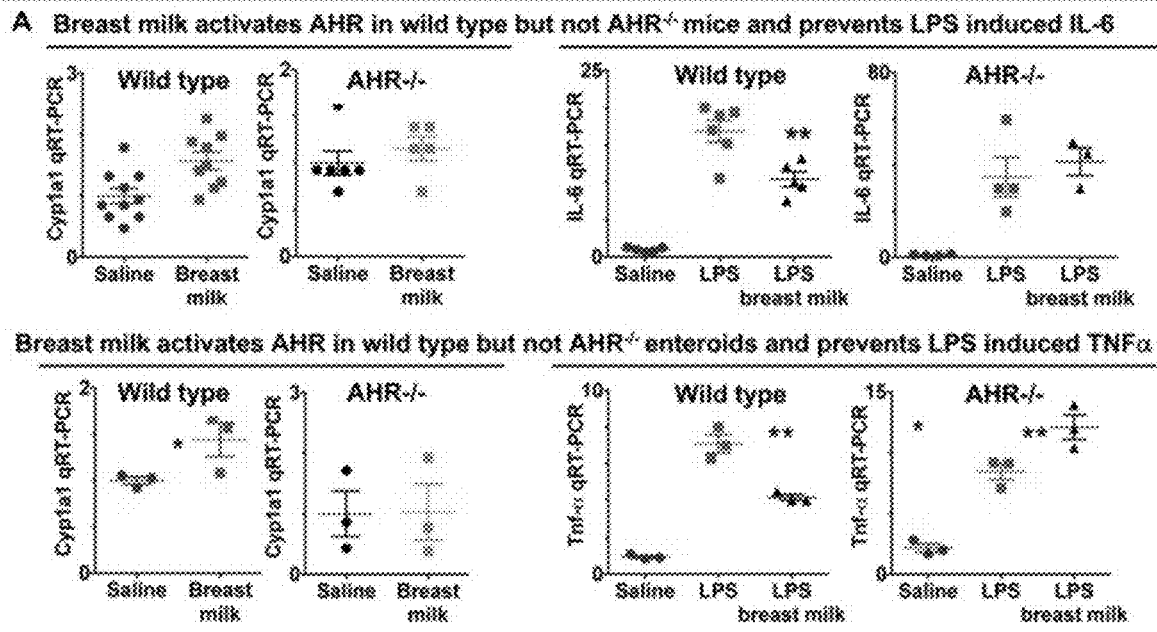
Figure 15B:
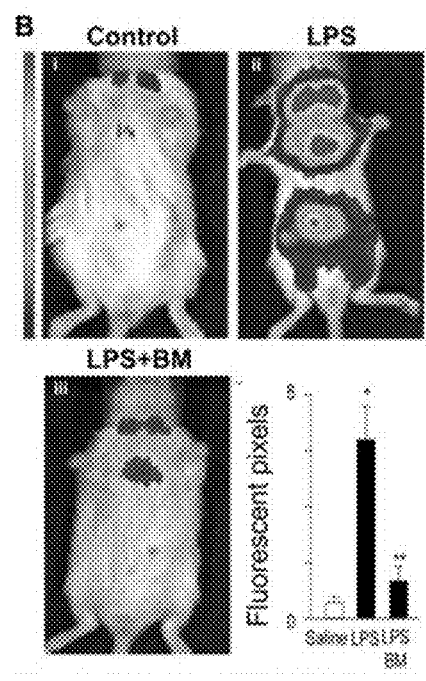
Figure 15C:
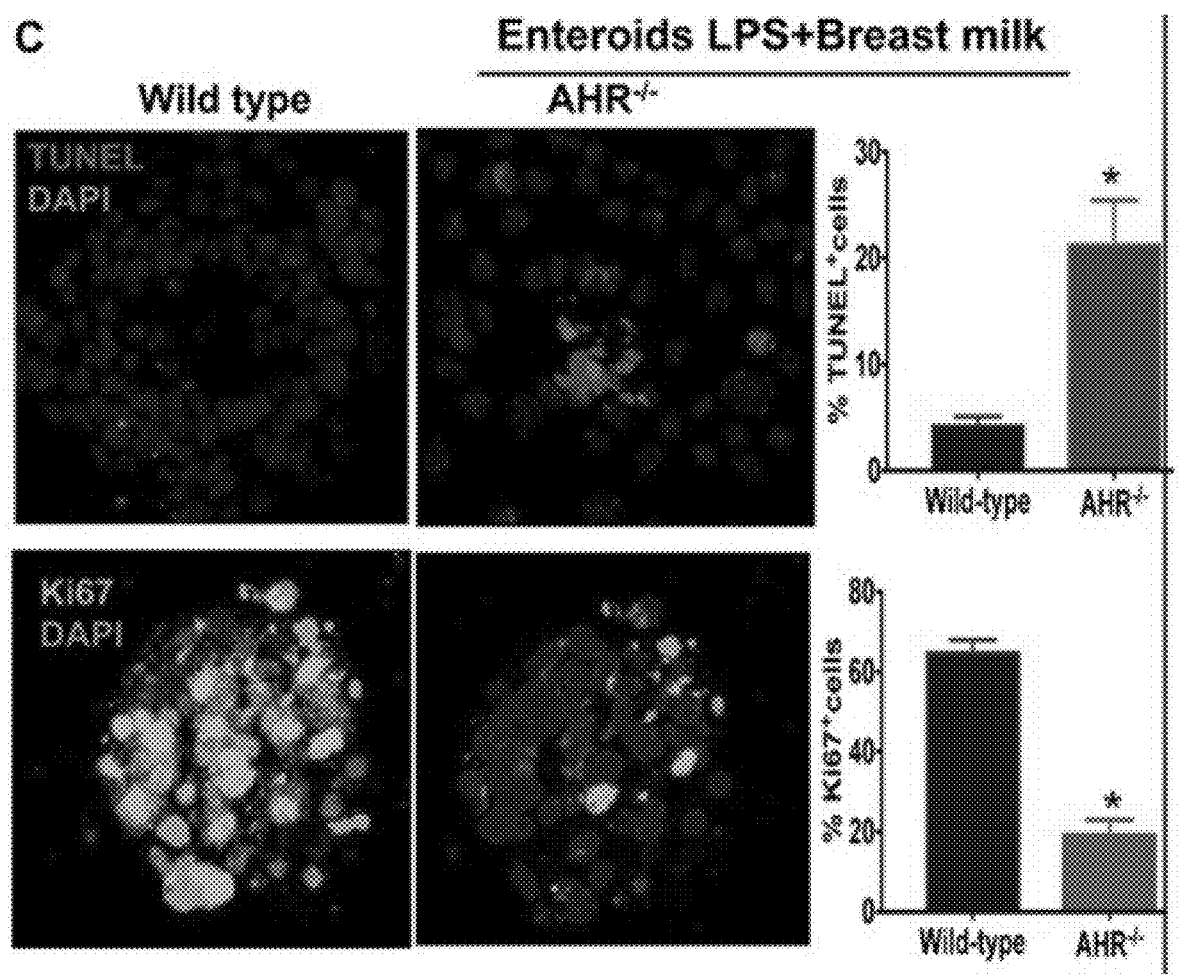
Figure 16A:
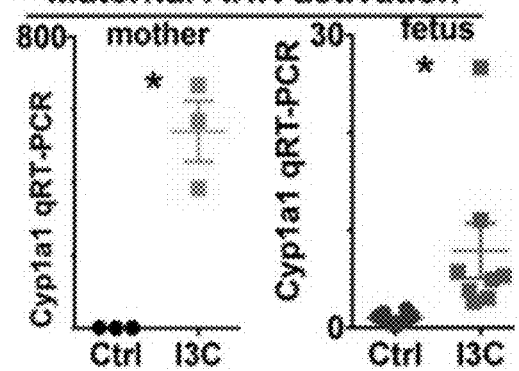
Figure 16B:
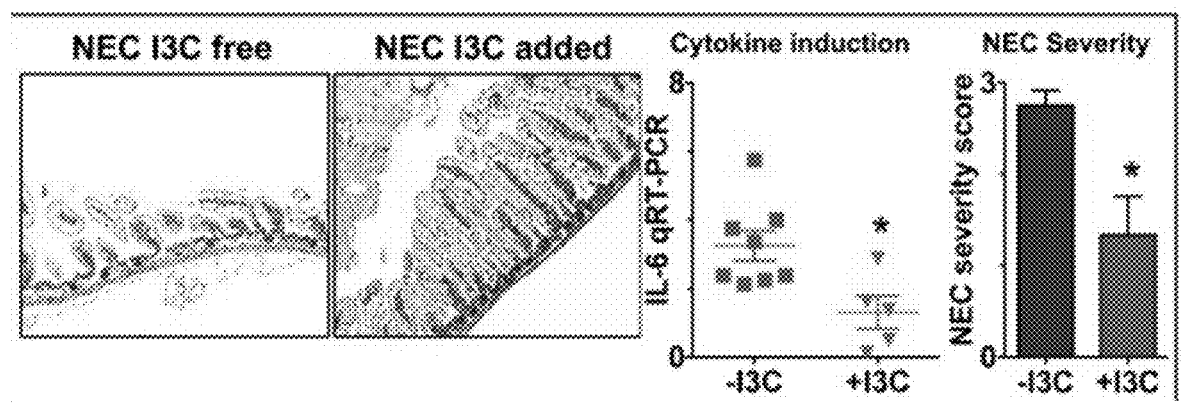
Figure 16C:
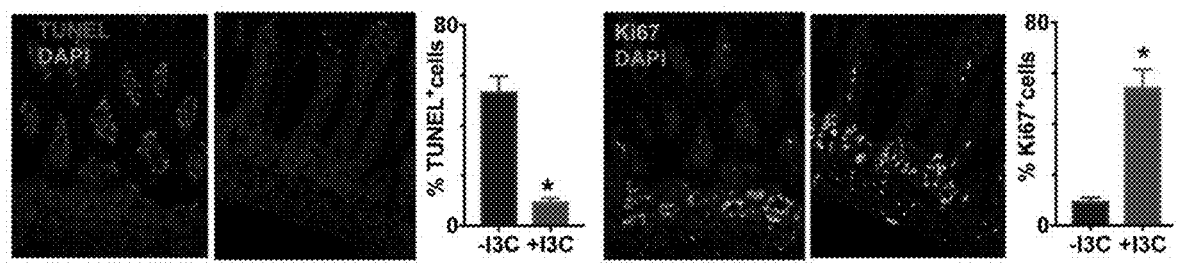
Figure 17A:
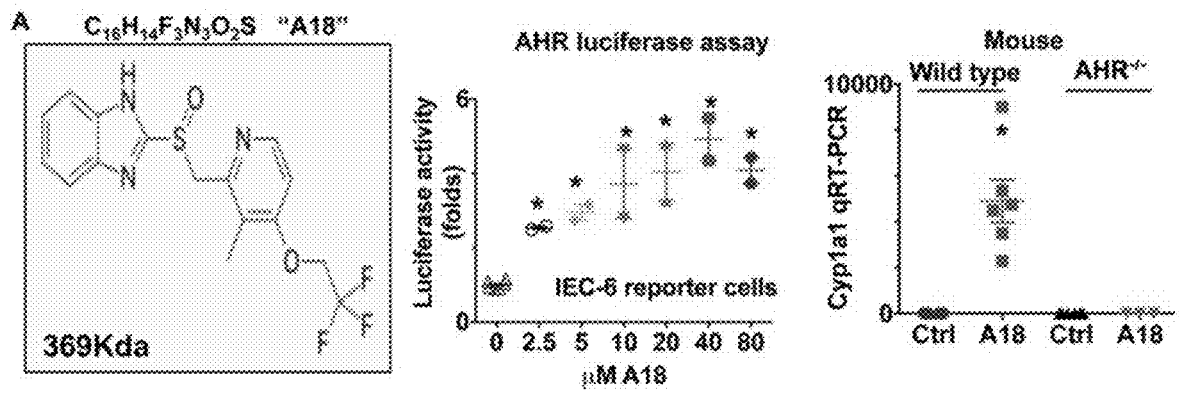
Figure 17B:
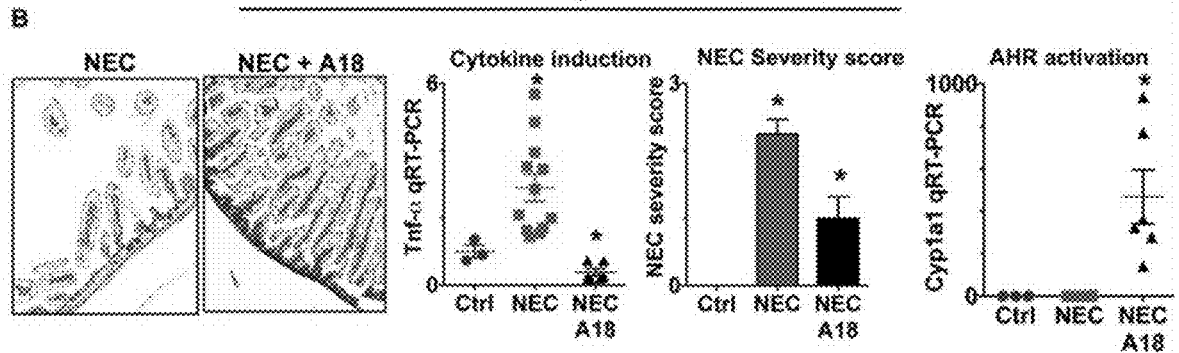
Figure 17C:
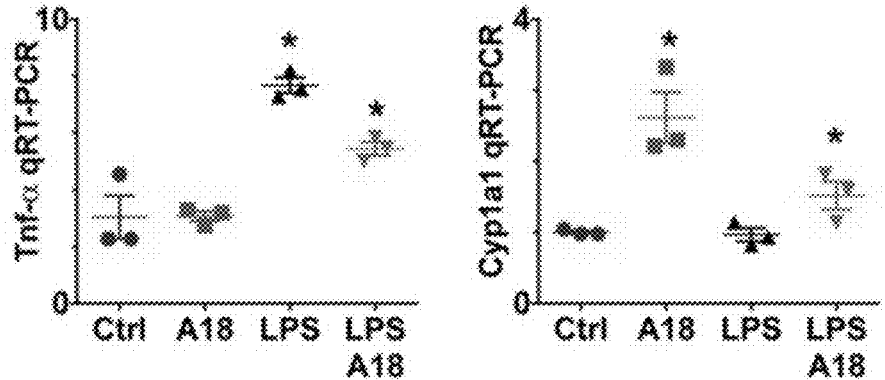
Figure 19:
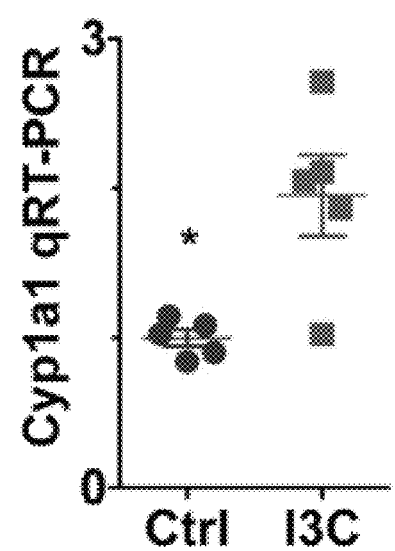
Figure 20:
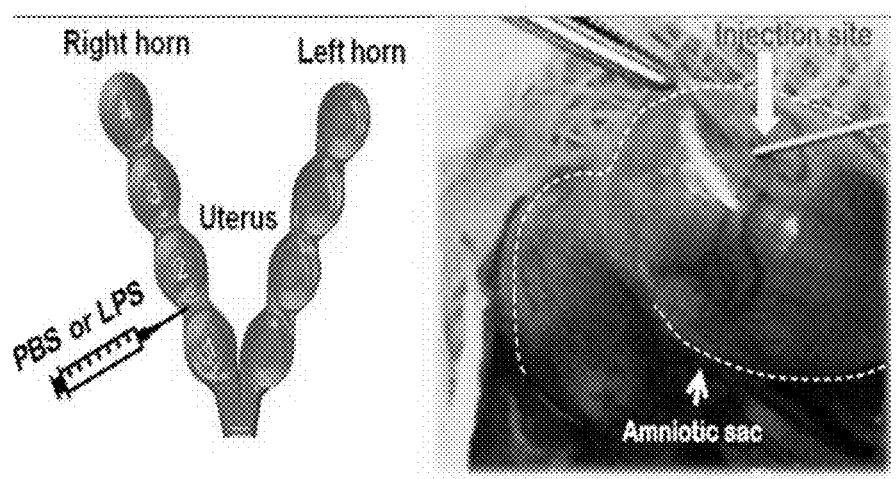
Figure 21A:
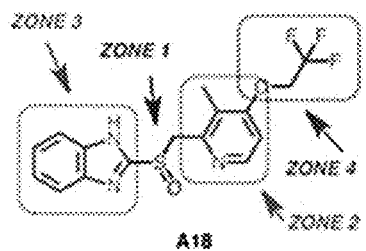
Figure 21B:
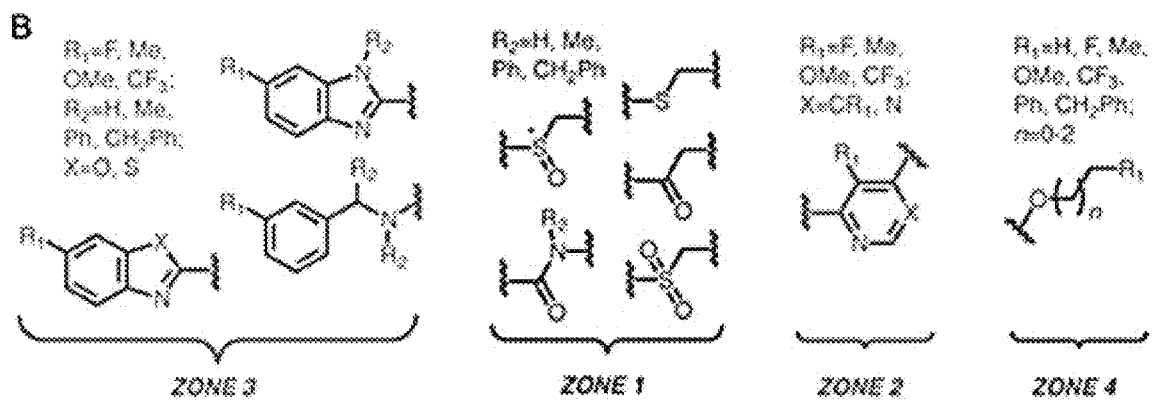
Figure 21C:
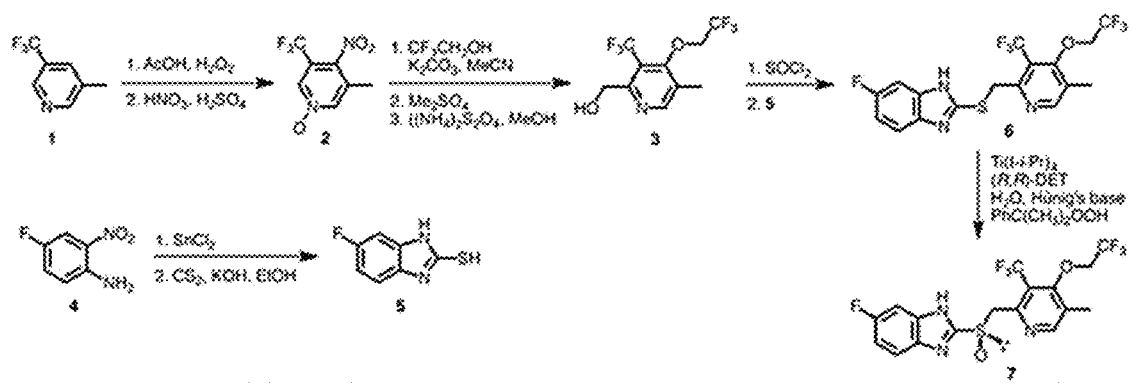
Figure 22:
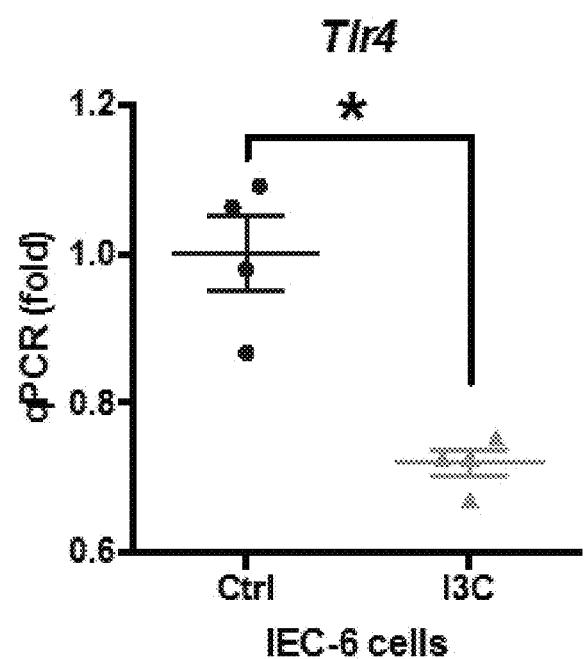
Figure 23:
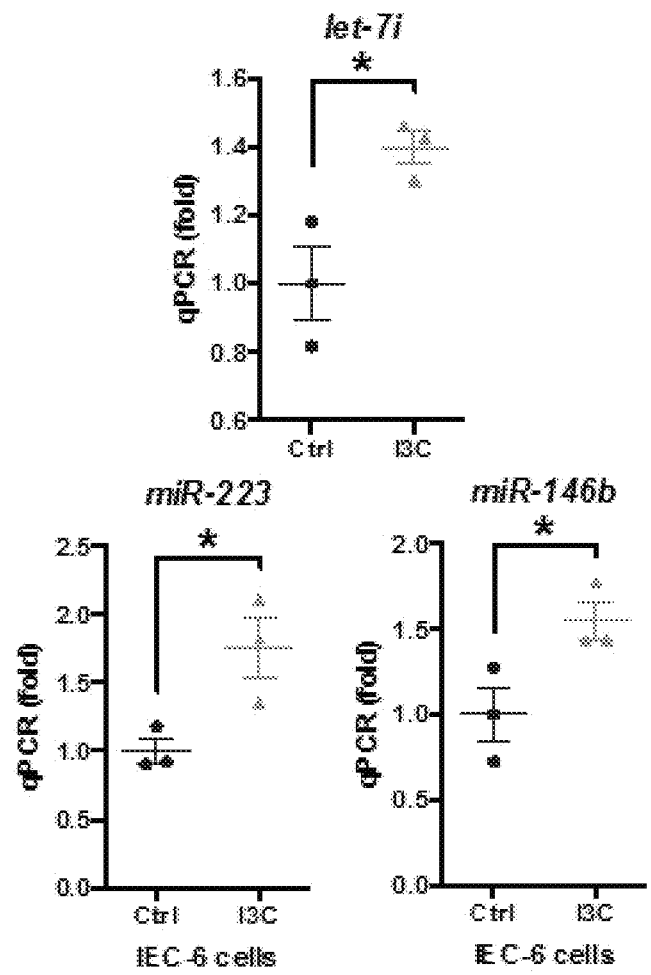
Figure 24:
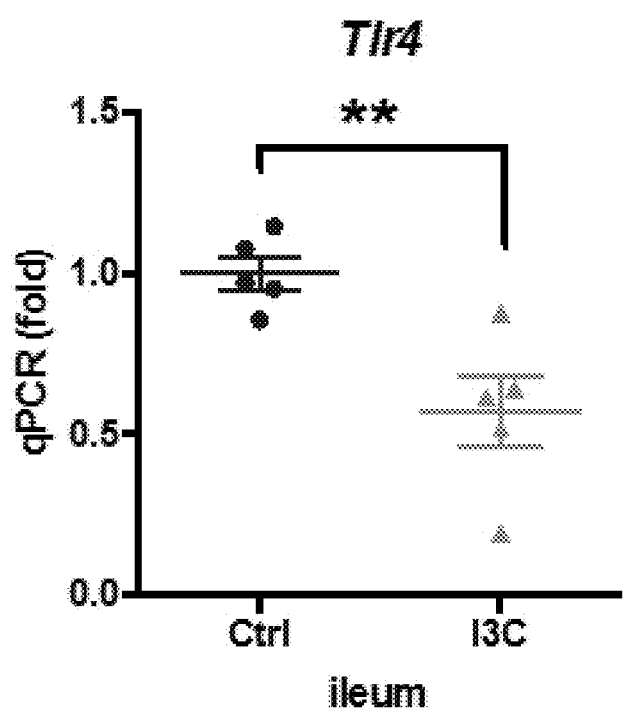
Figure 25:
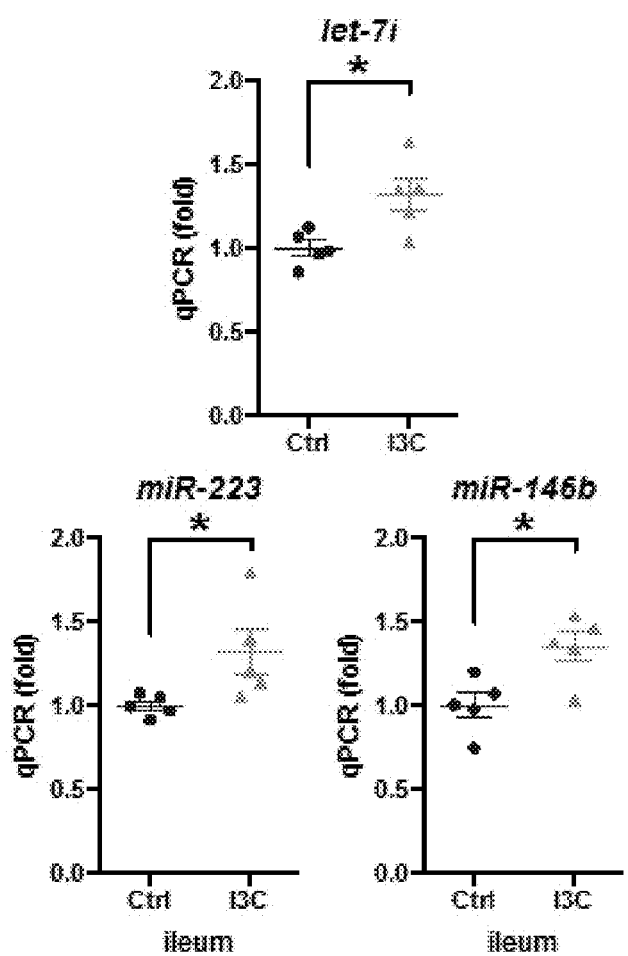

Having thus described the presently disclosed subject matter in general terms, reference will now be made to the accompanying Figures, which are not necessarily drawn to scale, and wherein:

FIG. 1 illustrates the AHR signaling pathway in the ileum of mice with NEC;

FIG. 2 illustrates the expression of proinflammatory cytokine Tnf in the ileum of mice with NEC;

FIG. 3 illustrates the expression of proinflammatory cytokine IL-6 in the ileum of mice with NEC;

FIG. 4 illustrates the expression of NEC marker S100a8 in the ileum of mice with NEC;

FIG. 5 illustrates the expression of NEC marker Lcn2 in the ileum of mice with NEC;

FIG. 6 illustrates the expression of NEC marker iFabp in the ileum of mice with NEC;

FIG. 7 illustrates the AHR signaling pathway in the ileum of mice with NEC whose mother was administered I3C from embryonic age 7 of the fetus until postnatal day 7;

FIG. 8 illustrates the expression of proinflammatory cytokine Tnf in the ileum of mice with NEC whose mother was administered I3C from embryonic age 7 of the fetus until postnatal day 7;

FIG. 9 illustrates the expression of proinflammatory cytokine IL-6 in the ileum of mice with NEC whose mother was administered I3C from embryonic age 7 of the fetus until postnatal day 7;

FIG. 10A, FIG. 10B, FIG. 10C, FIG. TOD, and FIG. TOE illustrate that TLR4 signaling in the intestinal epithelium is required for NEC development: (FIG. 10A) TLR4 SDS-PAGE in control and NEC mice and human ileum; (FIG. 10B and FIG. 10C) histological and gross morphology of wild-type, TLR4$^{-/-}$ or TLR4$^{\Delta IEC}$ mice in ctrl and NEC; (FIG. TOD), human control and NEC bowel; and (FIG. TOE) IL-1β in mouse and human NEC intestine. ***p<0.001 vs. control; 3 separate experiments; each dot=individual subject;

FIG. 11A, FIG. 11B, FIG. 11C, FIG. 11D, FIG. 11E, FIG. 11F, FIG. 11G, FIG. 11H, FIG. 11I, and FIG. 11J illustrate that TLR4 signaling in the intestinal epithelium causes reduced proliferation and increased apoptosis in NEC. Confocal micrographs from wild type and TLR4$^{\Delta IEC}$ control and NEC mice stained for the proliferation marker PCBA (FIG. 11A, FIG. 11B, FIG. 11C, and FIG. 11D) and the apoptosis marker TUNEL (FIG. 11E, FIG. 11F, FIG. 11G, and FIG. 11H). Quantification FIG. 11I, and FIG. 11J; ***p<005 vs. control; 5 separate experiments;

FIG. 12 illustrates expression of TLR4 in the prenatal and postnatal intestine in subjects/group; *p<0.05 vs. control, *p<0.01 vs e19;

FIG. 13A, FIG. 13B, FIG. 13C, FIG. 13D, and FIG. 13E illustrate signaling via the Aryl Hydrocarbon Receptor (AHR) in the intestinal epithelium prevents NEC: (FIG. 13A) confocal images of AHR expression on the intestinal epithelium in wild type and AHR$^{\Delta IEC}$ mice; (FIG. 13B) AHR ontogeny and expression in NEC; (FIG. 13C) AHR$^{\Delta IEC}$ but not AHR$^{\Delta Leuk}$ have severe NEC; (FIG. 13D) I3C does not protect in AHR$^{-/-}$; and (FIG. 13E) I3C reduces NEC severity in wild-type mice; three experiments; ***p<0.0001, *p<0.05, **p<0.01 between groups by t-test or ANOVA;

FIG. 14A, FIG. 14B, FIG. 14C, and FIG. 14D illustrate that AHR activation by indole-3-carbinole (I3C) reduces TLR4 signaling in the intestinal epithelium. (FIG. 14A) mouse enteroid; I3C treatment of enteroids reduces TNF and induces Cyp1a1; (FIG. 14B) I3C reduces LPS-induced IL-6 and increases Cyp1a1 in wild-type but not AHR$^{\Delta IEC}$ gut; (FIG. 14C) increases TLR4 expression and LPS signaling in AHR$^{-/-}$ and not AHR$^{\Delta IEC}$ mice vs. wild type; and (FIG. 14D) I3C reverses LPS induced apoptosis and impaired proliferation; three experiments. *p<0.05, p<0.01, *p<0.001;

FIG. 15A, FIG. 15B, and FIG. 15C illustrate that breast milk inhibits TLR4 via activation of AHR. (FIG. 15A) expression of Cyp1a1 and LPS induced IL-6 or TNFα in wild-type and AHR$^{-/-}$ mice and enteroids treated with breast milk or saline; (FIG. 15B) NFkB luciferase reporter mice treated with LPS and/or breast milk; (FIG. 15C) apoptosis (TUNEL) and proliferation (Ki67) in enteroids from wild type and AHR$^{-/-}$ mice treated with LPS and breast milk; three separate experiments; *p<0.05, **P<0.01;

FIG. 16A, FIG. 16B, and FIG. 16C illustrate that the administration of the AHR ligand I3C to the pregnant mother prevents NEC in the newborn mouse pup: (FIG. 16A) Cyp1a1 expression in the ileum of mother and fetus after oral I3C during pregnancy; (FIG. 16B, FIG. 16C) H&E, IL-6 qPCR, NEC severity scores, H&E, apoptosis (TUNEL) and proliferation (ki67) in the intestinal mucosa of mice after administration of saline or I3C to the mother. Three separate experiments. *p<0.05;

FIG. 17A, FIG. 17B, and FIG. 17C illustrate that the discovery of a novel AHR ligand ("A18") whose oral administration prevents NEC in mice and reduces TLR4 signaling in human tissue ex vivo: (FIG. 17A, left panel) A18; (FIG. 17A, mid panel) AHR-luciferase reporter assay; (FIG. 17A, right panel) A18 activates AHR in wild-type but not AHR$^{-/-}$ mice; (FIG. 17B) histology, TNF qRT-PCR, NEC severity, and Cypla1 in mice with NEC after A18; and (FIG. 17C) TNF and Cypla1 in human ileum after ex vivo LPS and/or A18. Three experiments; *p0.05;

FIG. 18A, FIG. 18B, FIG. 18C, FIG. 18D, and FIG. 18E illustrate in utero injection of fluorescent dye into the lumen of the fetal gut; knockdown of TLR4 but not STAT3 by TLR4 shRNA; *p<0.05 vs. saline;

FIG. 19 illustrates AHR in the intestine of pups administered breast milk from mothers administered control or I3C-rich milk;

FIG. 20 illustrates the location of intra-uterine injection between the $1^{st}$ and $2^{nd}$ uterine horns in pregnant mice;

FIG. 21A, FIG. 21B, and FIG. 21C illustrate the structure-activity relationship for analog preparation based on a zone model of A18;

FIG. 22 illustrates Tlr4 mRNA expression in IEC-6 cells treated with I3C. *p<0.05;

FIG. 23 illustrates let-7i, miR-223, and miR-146b in IEC-6 cells treated with 13C. *p<0.05;

FIG. 24 illustrates Tlr4 mRNA expression in the ileum of mice treated with 13C. *p<0.05; and FIG. 25 illustrates the expression of let-7i, miR-223, and miR-146b in the ileum of mice treated with I3C.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Aryl Hydrocarbon Receptor (AHR) Agonists for the Prevention and Treatment of Inflammatory Disorders In seeking to understand the mechanisms leading to the development of NEC, preliminary observations indicated that the aryl hydrocarbon receptor (AHR) plays a protective role in mice with NEC. This observation suggested the possibility that the discovery of AHR agonists may serve as novel therapeutic agents. To test this hypothesis, a mouse model of NEC, Sodhi et al., 2012, was been developed that involves the administration to newborn mice infant formula, intermittent hypoxia, and the stool of a patient with NEC, which after 4 days results in intestinal necrosis and systemic sepsis that mimics the human disease. Importantly, mice with NEC show reduced expression of the aryl hydrocarbon receptor (AHR) within the intestine, suggesting lack of AHR signaling may contribute to NEC pathogenesis.

The AHR is a protein that is activated by molecules within certain foods, such as green leafy vegetables, and other naturally occurring compounds. Gargaro et al., 2016. Further, mice lacking AHR exhibited severe NEC as manifested by intestinal disruption on histology and severe cytokine induction. Importantly, the administration of the known AHR ligand indole 3 cabinol (13C) to mice afflicted with NEC reduced the expression of proinflammatory gene IL-1, suggesting that agents which activate the AHR receptor may serve as novel therapeutic agents for the prevention or treatment of NEC.

Given that AHR is activated by components of certain foods, and given that the administration of infant formula plays a key role in NEC pathogenesis, Good et al., 2016, these findings lead to a novel approach for the treatment or prevention of NEC in children based on the design of novel infant formulas that contain AHR agonists. Based on these preliminary studies, a screen for potential AHR ligands was performed. Using an AHR-luciferase reporter system, a drug library was screened and compounds that were found to activate AHR were identified.

Accordingly, in some embodiments, the presently disclosed subject matter provides a method for treating or preventing or reducing the risk of an inflammatory disorder associated with a reduced expression of an aryl hydrocarbon receptor (AhR) in a subject in need of treatment thereof, the method comprising administering to the subject one or more AhR agonists, or pharmaceutically acceptable salts thereof, to activate the AhR, thereby treating or preventing or reducing the risk of the inflammatory disorder.

Inflammatory disorders include a large number of disorders or conditions that are involved in a variety of diseases, including those involving the immune system, including those demonstrated in allergic reactions and myopathies, or non-immune diseases with causal origins in inflammatory processes including, but not limited to cancer, atherosclerosis, and ischemic heart disease. Non-limiting examples of disorders associated with inflammation include, but are not limited to, acne vulgaris, asthma, autoimmune diseases, autoinflammatory diseases, celiac disease, chronic prostatitis, diverticulitis, glomerulonephritis, hidradenitis suppurativa, hypersensitivities, inflammatory bowel diseases, interstitial cystitis, otitis, pelvic inflammatory disease, reperfusion injury, rheumatic fever, rheumatoid arthritis, sarcoidosis, transplant rejection, and vasculitis.

More particularly, the presently disclosed subject matter may be used to treat any disease or disorder involving AhR activation, including, but not limited to, inflammatory disorders, such as necrotizing enterocolitis, inflammatory bowel disease, autoimmune diseases, Crohn's disease, celiac disease, ulcerative colitis, cardiovascular disease, ocular Behcet's disease, breast cancer, and others.

In particular embodiments, the inflammatory disorder is necrotizing enterocolitis.

As used herein, an agonist is an agent that binds to a receptor, e.g., AhR, and activates the receptor to produce a biological response.

In some embodiments, the one or more AhR agonists is selected from the group consisting of abacavir, abacavir sulfate, amlexanox, anagrelide hydrochloride, benzocaine (ethyl p-aminobenzoate), bromindione, catharanthine, dexlansoprazole, eseroline, febuxostat, helenien (xantofyl palmitate), hydralazine hydrochloride, indoprofen, ipratropium bromide, lansoprazole, menadione sodium bisulfate, nitazoxanide, omeprazole, phenazopyridine, phenazopyridine hydrochloride, primaquine, rabeprazole sodium, tenatoprazole, tranilast (sb 252218), and ziprasidone hydrochloride, indole-3-carbinol (I3C), A18, or derivatives and combinations thereof, or pharmaceutically acceptable salts thereof.

In particular embodiments, the one or more AhR agonists is selected from the group consisting of abacavir, lansoprazole, tranilast, and raberprazole, indole-3-carbinol (I3C), A18, or derivatives and combinations thereof, or pharmaceutically acceptable salts thereof.

Representative, non-limiting derivatives of I3C are disclosed in U.S. Pat. Nos. 6,001,868; 6,369,095; and U.S. Pat. No. 6,656,963 to Firestone et al., each of which is incorporated by reference in its entirety.

In yet more particular embodiments, the one or more AhR agonists is a compound of formula (I):

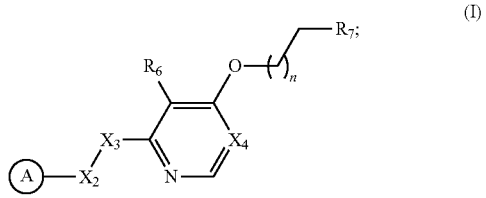

wherein:

n is an integer selected from the group consisting of 0, 1, and 2;

A is selected from the group consisting of:

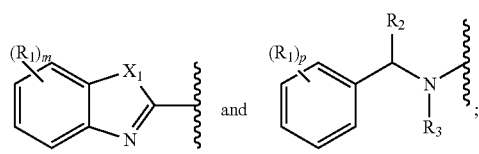

wherein:

m is an integer selected from the group consisting of 0, 1, 2, 3, and 4;

p is an integer selected from the group consisting of 0, 1, 2, 3, 4, and 5;

each $R_1$ is independently selected from the group consisting of H, $C_1$-$C_6$ alkyl, $C_1$-$C_6$ substituted alkyl, alkoxyl, halogen, and —$CF_3$;

$R_2$ and $R_3$ are each independently selected from the group consisting of H, $C_1$-$C_6$ alkyl, $C_1$-$C_6$ substituted alkyl, aryl, substituted aryl, heteroaryl, and benzyl;

$X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$X_2$ is selected from the group consisting of —S—, —S(=O)—, —S(=O)$_2$—, and —C(=O)—;

$X_3$ is selected from the group consisting of —$CH_2$— and —$NR_5$—, wherein $R_5$ is selected from the group consisting of H, $C_1$-$C_6$ alkyl, $C_1$-$C_6$ substituted alkyl, aryl, substituted aryl, heteroaryl, and benzyl;

$X_4$ is selected from the group consisting of —N— and —$CR_5$—, wherein $R_5$ is selected from the group consisting of H, $C_1$-$C_6$ alkyl, $C_1$-$C_6$ substituted alkyl, alkoxyl, halogen, and —$CF_3$;

$R_6$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$R_7$ is selected from the group consisting of H, $C_1$-$C_6$ alkyl, $C_1$-$C_6$ substituted alkyl, alkoxyl, halogen, —$CF_3$, aryl, substituted aryl, heteroaryl, and benzyl;

or pharmaceutically acceptable salts thereof.

In particular embodiments, the substituted alkyl or unsubstituted alkyl of formula (I) can be a $C_1$, $C_2$, $C_3$, $C_4$, $C_5$, or $C_6$, linear or branched alkyl, in some embodiments, $C_1$-4 substituted or unsubstituted alkyl, in some embodiments. $C_1$-$C_6$ substituted or unsubstituted alkyl, in some embodiments, CG, alkyl substituted or unsubstituted alky, including, but not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, and the like, each of which can include one or more substitutents. Representative substituent groups include, but are not limited to, alkyl, substituted alkyl, halogen, aryl, substituted aryl, alkoxyl, hydroxyl, nitro, amino, alkylamino, dialkylamino, sulfate, cyano, mercapto, and alkylthio.

In even yet more particular embodiments, the one or more AhR agonists is A18.

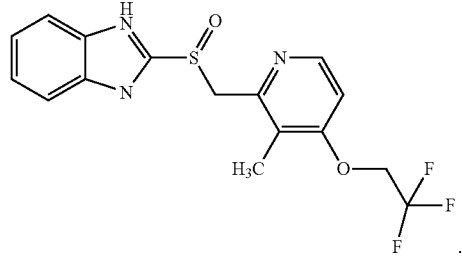

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In some embodiments, the subject is a human subject. In particular embodiments, the subject is an infant. As used herein, the term "infant" can refer to a child from about one month after birth to one year after birth and can include a child up to about two years after birth.

As used herein, the term "newborn" or "neonate" refers to an infant in the first 28 days after birth, and can be an infant only a few hours after birth, a few days after birth, or up to a month after birth. The term applies generally to premature, full term (e.g., 38 weeks and beyond), and post mature infants.

In yet more particular embodiments, the human subject is a premature infant. As used herein, the term "premature birth" or "preterm birth" refers to the birth of a baby at fewer than 37 weeks gestational age and can include babies born at 37 weeks, 36 weeks, 35 weeks, 34 weeks, 33 weeks, 32 weeks, 31 weeks, 30 weeks, 29 weeks, 28 weeks, 27 weeks, 26 weeks, 25 weeks, 24 weeks, 23 weeks, 22 weeks, 21 weeks, and 20 weeks gestational age.

As used herein, "treatment" includes, without limitation, (1) decreasing the level of one or more index of inflammation (e.g., inflammatory cytokines, such as TNF-α, IL-6, IL-12p40, IL-1β); (2) decreasing a clinical marker of inflammation, such as S100a8, Lcn2, iFabp, leukocyte count, fever, hypotension; and/or (3) reducing the risk of an adverse outcome, such as death, organ failure, hypoxia, or the need for surgery. "Treatment" does not necessarily mean that the condition being treated will be cured. A "therapeutically effective amount" of an AhR agonist achieves treatment.

"Reducing the risk" or "reducing the severity of" does not necessarily mean that the subject being treated will not develop NEC. A "prophylactically effective amount" for preventing NEC reduces the risk of NEC by at least about ⅕ or by at least about ⅓. Any infant may be eligible for such prophylactic treatment. Infants at higher risk for NEC as a result of premature birth or low birth rate may particularly benefit, as well as a term infant otherwise at risk for NEC Further, "methods of preventing" are defined as methods which reduce the risk of developing the disease, and do not necessarily result in 100% prevention of the disease. As such, these methods, applied prophylactically to an infant, may not only reduce the risk, but may also reduce the severity of the disease if it does occur. By definition, such preventative methods may be administered to an infant having no signs of preexisting NEC as well as to an infant which is exhibiting one or more early clinical sign consistent with NEC but in which a definitive diagnosis of NEC has not been established.

In some embodiments, the administration is enteral administration. As used herein, the term "enteral administration" includes feeding or drug administration through the gastrointestinal (GI) tract. Enteral administration can include oral administration or gastric administration, for example, via a feeding tube through the nasal passage, i.e., a nasogastric (NG) tube, or a feeding tube leading directly to the stomach, i.e., a percutaneous endoscopic gastrostomy (PEG) tube.

II. Infant Nutritional Formula Comprising Aryl Hydrocarbon Receptor (Ahr) Agonists for the Prevention and Treatment of Inflammatory Disorders In some embodiments, the presently disclosed subject matter provides an infant nutritional formula comprising a therapeutically effective amount of one or more aryl hydrocarbon receptor (AhR) agonists, or pharmaceutically acceptable salts thereof.

In some embodiments, the one or more AhR agonists is selected from the group consisting of abacavir, abacavir sulfate, amlexanox, anagrelide hydrochloride, benzocaine (ethyl p-aminobenzoate), bromindione, catharanthine, dexlansoprazole, eseroline, febuxostat, helenien (xantofyl palmitate), hydralazine hydrochloride, indoprofen, ipratropium bromide, lansoprazole, menadione sodium bisulfate, nitazoxanide, omeprazole, phenazopyridine, phenazopyridine hydrochloride, primaquine, rabeprazole sodium, tenatoprazole, tranilast (sb 252218), and ziprasidone hydrochloride, indole-3-carbinol (I3C), A18, or derivatives and combinations thereof, or pharmaceutically acceptable salts thereof.

In particular embodiments, the one or more AhR agonists is selected from the group consisting of abacavir, lansoprazole, tranilast, and raberprazole, indole-3-carbinol (I3C), A18, or derivatives and combinations thereof, or pharmaceutically acceptable salts thereof.

Representative, non-limiting derivatives of I3C are disclosed in U.S. Pat. Nos. 6,001,868; 6,369,095; and U.S. Pat. No. 6,656,963 to Firestone et al., each of which is incorporated by reference in its entirety.

In yet more particular embodiments, the one or more AhR agonists is a compound of formula (I):

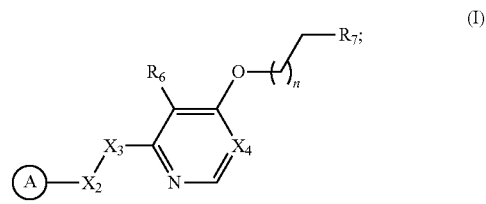

wherein:
n is an integer selected from the group consisting of 0, 1, and 2;
a is selected from the group consisting of:

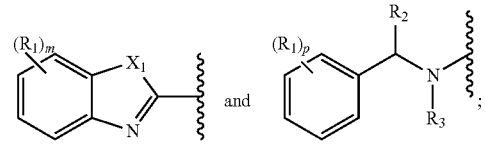

wherein:
m is an integer selected from the group consisting of 0, 1, 2, 3, and 4;
p is an integer selected from the group consisting of 0, 1, 2, 3, 4, and 5;
each $R_1$ is independently selected from the group consisting of H, $C_1$-$C_6$ alkyl, $C_1$-$C_6$ substituted alkyl, alkoxyl, halogen, and —$CF_3$;
$R_2$ and $R_3$ are each independently selected from the group consisting of H, $C_1$-$C_6$ alkyl, $C_1$-$C_6$ substituted alkyl, aryl, substituted aryl, heteroaryl, and benzyl;
$X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;
$X_2$ is selected from the group consisting of —S—, —S(=O)—, —S(=O)$_2$—, and —C(=O)—;

$X_3$ is selected from the group consisting of —$CH_2$— and —$NR_5$—, wherein $R_5$ is selected from the group consisting of H, $C_1$-$C_6$ alkyl, $C_1$-$C_6$ substituted alkyl, aryl, substituted aryl, heteroaryl, and benzyl;

$X_4$ is selected from the group consisting of —N— and —$CR_5$—, wherein $R_5$ is selected from the group consisting of H, $C_1$-$C_6$ alkyl, $C_1$-$C_6$ substituted alkyl, alkoxyl, halogen, and —$CF_3$;

$R_6$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$R_7$ is selected from the group consisting of H, $C_1$-$C_6$ alkyl, $C_1$-$C_6$ substituted alkyl, alkoxyl, halogen, —$CF_3$, aryl, substituted aryl, heteroaryl, and benzyl;

or pharmaceutically acceptable salts thereof.

In particular embodiments, the substituted alkyl or unsubstituted alkyl of formula (I) can be a $C_1$, $C_2$, $C_3$, $C_4$, OF $C_6$, linear or branched alkyl, in some embodiments. $C_1$-$C_4$ substituted or unsubstituted alkyl, in some embodiments. $C_1$-$C_6$ substituted or unsubstituted alkyl, in some embodiments, $C_1$-$C_6$ alkyl substituted or unsubstituted alkyl, including, but not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, and the like, each of which can include one or more substitutents. Representative substituent groups include, but are not limited to, alkyl, substituted alkyl, halogen, aryl, substituted aryl, alkoxyl, hydroxyl, nitro, amino, alkylamino, dialkylamino, sulfate, cyano, mercapto, and alkylthio.

In even yet more particular embodiments, the one or more AhR agonists is A18:

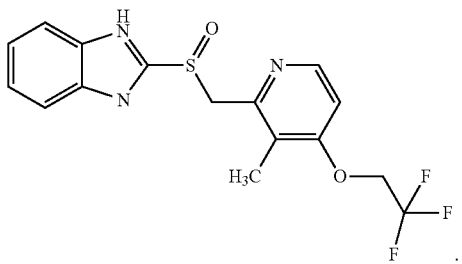

In certain embodiments, the formula is nutritionally complete, that is it is suitable as a sole source of nutrition for a premature or full term infant. In such embodiments, the formula comprises one or more ingredients selected from the group consisting of protein, fat, one or more fatty acids, such as linoleic acid, and/or oleic acid, and/or other fatty acids, vitamin A, vitamin C, vitamin D, vitamin E, vitamin K, thiamin (B1), riboflavin (B2), B6, B12, niacin, folic acid, pantothenic acid, calcium, magnesium, iron, zinc, manganese, copper, phosphorous, iodine, sodium chloride, potassium chloride, one or more carbohydrates, such as oligosaccharides, such as milk oligosaccharides, and other complex or simple sugars, including lactose, sucrose, glucose, dextrins, natural and modified starches, cholesterol, phospholipid, casein, whey, soy protein, nucleotides, emulsifiers, stabilizers, and diluents.

In some embodiments, the formula is in the form of a liquid, a powder, a capsule, a tablet, or an orally disintegrating tablet. In particular embodiments, the liquid is in the form of a solution, an emulsion, or a suspension.

In certain embodiments, where the formulation is a liquid, the formulation comprises a pharmaceutically suitable liquid such as, but not limited to, water, saline, or an emulsion formed between an aqueous solution and an oil or other liquid that is not substantially miscible with water. In a specific non-limiting embodiment a liquid formulation may comprise a hydrophobic compound as well as an emulsifier.

In certain non-limiting embodiments, one or more AhR agonists can be added to a commercial infant nutritional formula prior to administration, for example, but not limited to, Similac®, Enfamil® or Gerber® formulas. In specific non-limiting embodiments such formula may be Similac® Premature Infant Formula, Enfamil® Premature LIPIL, or Gerber® Good Start, or similar commercially available infant formulas formulated for premature infants.

In other embodiments, the one or more AhR agonists can be included in an infant nutritional formula that has not yet been commercially available, where the infant nutritional formula further comprises one or more nutrients, such as proteins, lipids, carbohydrates, electrolytes, and/or vitamins as provided hereinabove. The infant nutritional formula may be, without limitation, a liquid or a powder for reconstitution with liquid.

In one specific non-limiting embodiment the one or more AhR agonists may be added to other components of the formulation shortly prior to use, for example within 24 hours or within 6 hours or within 2 hours or within 1 hour of use. In certain embodiments, the formula is adapted for enteral administration to an infant. In more certain embodiments, the enteral administration is oral administration or gastric administration.

III. Maternal Administration of an Aryl Hydrocarbon Receptor (Ahr) Agonist

In some embodiments, the presently disclosed subject matter provides a method for preventing, reducing the risk of, or reducing the severity of an inflammatory disorder associated with a reduced expression of an aryl hydrocarbon receptor (AhR) in a subject in need of treatment thereof, the method comprising administering to a mother while pregnant with the subject one or more AhR agonists, or pharmaceutically acceptable salts thereof, to activate the AhR, thereby treating or preventing, reducing the risk of, or reducing the severity of the inflammatory disorder.

In some embodiments, the mother is at risk for delivering the subject prematurely.

In some embodiments, the one or more AhR agonists is selected from the group consisting of abacavir, abacavir sulfate, amlexanox, anagrelide hydrochloride, benzocaine (ethyl p-aminobenzoate), bromindione, catharanthine, dexlansoprazole, eseroline, febuxostat, helenien (xantofyl palmitate), hydralazine hydrochloride, indoprofen, ipratropium bromide, lansoprazole, menadione sodium bisulfate, nitazoxanide, omeprazole, phenazopyridine, phenazopyridine hydrochloride, primaquine, rabeprazole sodium, tenatoprazole, tranilast (sb 252218), and ziprasidone hydrochloride, indole-3-carbinol (I3C), A18, or derivatives and combinations thereof, or pharmaceutically acceptable salts thereof.

In particular embodiments, the one or more AhR agonists is selected from the group consisting of abacavir, lansoprazole, tranilast, and raberprazole, indole-3-carbinol (I3C), A18, or derivatives and combinations thereof, or pharmaceutically acceptable salts thereof.

Representative, non-limiting derivatives of I3C are disclosed in U.S. Pat. Nos. 6,001,868; 6,369,095; and U.S. Pat.

No. 6,656,963 to Firestone et al., each of which is incorporated by reference in its entirety.

In yet more particular embodiments, the one or more AhR agonists is a compound of formula (I):

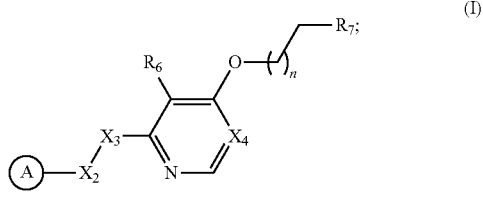

wherein:

n is an integer selected from the group consisting of 0, 1, and 2;

A is selected from the group consisting of:

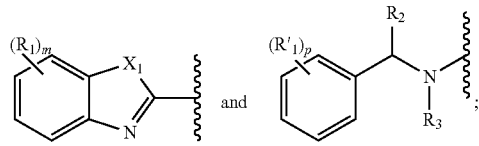

wherein:

m is an integer selected from the group consisting of 0, 1, 2, 3, and 4;

p is an integer selected from the group consisting of 0, 1, 2, 3, 4, and 5;

each $R_1$ is independently selected from the group consisting of H, $C_1$-$C_6$ alkyl, $C_1$-$C_6$ substituted alkyl, alkoxyl, halogen, and —$CF_3$;

$R_2$ and $R_3$ are each independently selected from the group consisting of H, $C_1$-$C_6$ alkyl, $C_1$-$C_6$ substituted alkyl, aryl, substituted aryl, heteroaryl, and benzyl;

$X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$X_2$ is selected from the group consisting of —S—, —S(=O)—, —S(=O)$_2$—, and —C(=O)—;

$X_3$ is selected from the group consisting of —$CH_2$— and —$NR_5$—, wherein $R_5$ is selected from the group consisting of H, $C_1$-$C_6$ alkyl, $C_1$-$C_6$ substituted alkyl, aryl, substituted aryl, heteroaryl, and benzyl;

$X_4$ is selected from the group consisting of —N— and —$CR_5$—, wherein $R_5$ is selected from the group consisting of H, $C_1$-$C_6$ alkyl, $C_1$-$C_6$ substituted alkyl, alkoxyl, halogen, and —$CF_3$;

$R_6$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$R_7$ is selected from the group consisting of H, $C_1$-$C_6$ alkyl, $C_1$-$C_6$ substituted alkyl, alkoxyl, halogen, —$CF_3$, aryl, substituted aryl, heteroaryl, and benzyl; or pharmaceutically acceptable salts thereof.

In particular embodiments, the substituted alkyl or unsubstituted alkyl of formula (I) can be a $C_1$, $C_2$, $C_3$, $C_4$, $C_5$, or $C_6$, linear or branched alkyl, in some embodiments. $C_1$-4 substituted or unsubstituted alkyl, in some embodiments. $C_1$-6 substituted or unsubstituted alkyl, in some embodiments, CG, alkyl substituted or unsubstituted alkyl including, but not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, and the like, each of which can include one or more substitutents. Representative substituent groups include, but are not limited to, alkyl, substituted alkyl, halogen, aryl, substituted aryl, alkoxyl, hydroxyl, nitro, amino, alkylamino, dialkylamino, sulfate, cyano, mercapto, and alkylthio.

In even yet more particular embodiments, the one or more AhR agonists is A18:

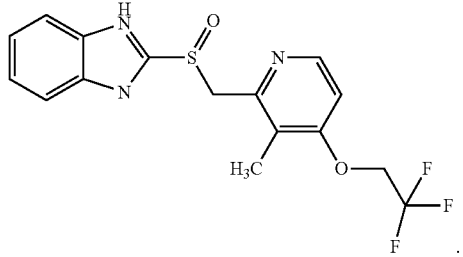

IV. Ahr Agonists of Formula (I)

In some embodiments, the presently disclosed subject matter provides an AhR agonist of formula (I):

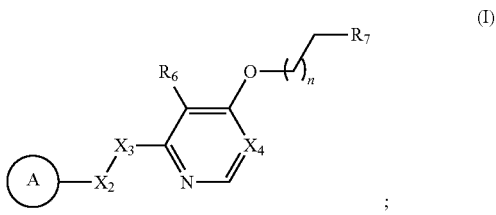

wherein:

n is an integer selected from the group consisting of 0, 1, and 2;

A is selected from the group consisting of

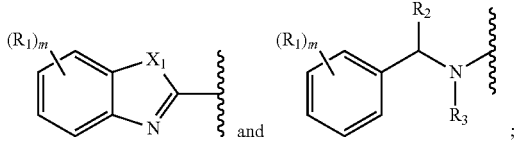

wherein:

m is an integer selected from the group consisting of 0, 1, 2, 3, and 4;

p is an integer selected from the group consisting of 0, 1, 2, 3, 4, and 5;

$R_1$ is selected from the group consisting of $C_1$-$C_6$ alkyl, $C_1$-$C_6$ substituted alkyl, alkoxyl, halogen, and —$CF_3$;

$R'_1$ is selected from the group consisting of H, $C_1$-$C_6$ alkyl, $C_1$-$C_6$ substituted alkyl, alkoxyl, halogen, and —$CF_3$;

$R_2$ and $R_3$ are each independently selected from the group consisting of H, $C_1$-$C_6$ alkyl, $C_1$-$C_6$ substituted alkyl, aryl, substituted aryl, heteroaryl, and benzyl;

$X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;

$X_2$ is selected from the group consisting of —S—, —S(=O)—, —S(=O)$_2$—, and —C(=O)—;

$X_3$ is selected from the group consisting of —CH$_2$— and —NR$_5$—, wherein R$_5$ is selected from the group consisting of H, C$_1$-C$_6$ alkyl, C$_1$-C$_6$ substituted alkyl, aryl, substituted aryl, heteroaryl, and benzyl;

$X_4$ is selected from the group consisting of —N— and —CR$_5$—, wherein R$_5$ is selected from the group consisting of H, C$_1$-C$_6$ alkyl, C$_1$-C$_6$ substituted alkyl, alkoxyl, halogen, and —CF$_3$;

$R_6$ is selected from the group consisting of O, S, and NR$_4$, wherein R$_4$ is selected from the group consisting of H, C$_1$-C$_6$ alkyl, C$_1$-C$_6$ substituted alkyl, aryl, substituted aryl, heteroaryl, and benzyl;

$R_7$ is selected from the group consisting of H, C$_1$-C$_6$ alkyl, C$_1$-C$_6$ substituted alkyl, alkoxyl, halogen, —CF$_3$, aryl, substituted aryl, heteroaryl, and benzyl; or pharmaceutically acceptable salts thereof.

V. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position.

The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_{1-10}$ means one to ten carbons, including 1, 2, 3, 4, 5, 6, 7, 8, 9, and 10 carbons). In particular embodiments, the term "alkyl" refers to C$_1$-20 inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_1$-s straight-chain alkyls. In other embodiments, "alkyl" refers, in particular, to $C_1$-s branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxy, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl.

Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like.

Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds.

Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule.

Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

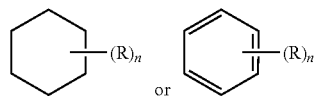

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

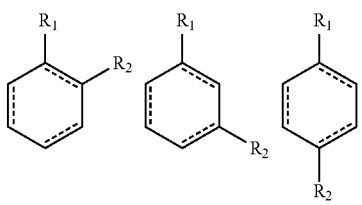

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ($\sim$) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN, CF$_3$, fluorinated C$_{1-4}$ alkyl, and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl.

Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_1$-20 inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure—NHR' wherein R" is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S($O_2$)R.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms.

Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

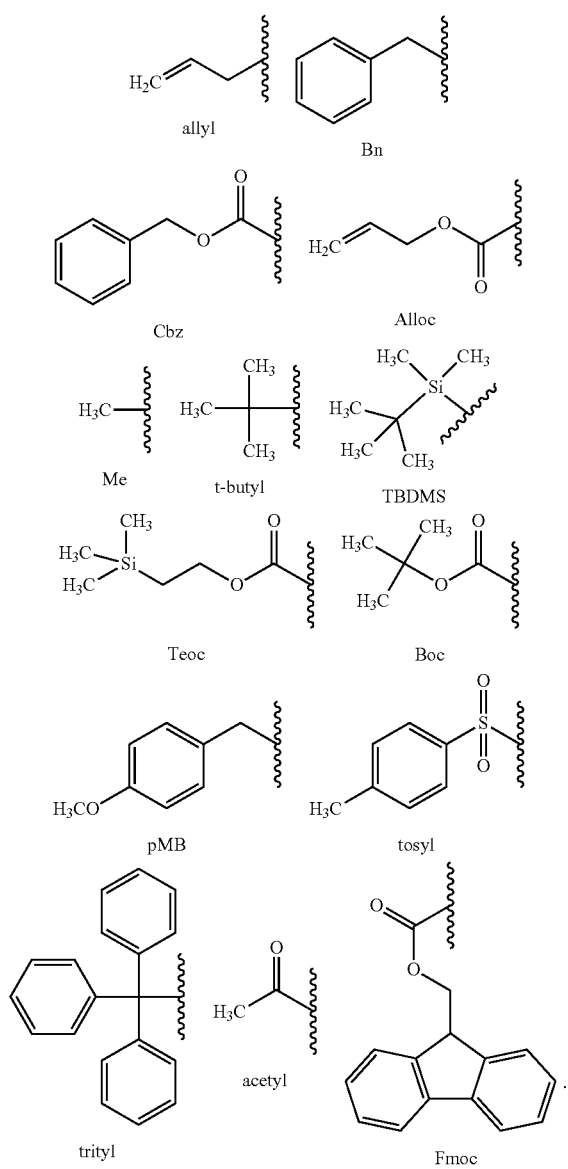

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, +100% in some embodiments+50%, in some embodiments+20%, in some embodiments+10%, in some embodiments+5%, in some embodiments+1%, in some embodiments+0.5%, and in some embodiments+0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Experimental Design

Necrotizing enterocolitis (NEC) was induced in 7-day-old mouse pups by gavage feeding and hypoxia exposure for 4 days in presence of abacavir, lansoprazole, tranilast and raberprazole. The ileum was harvested at the end of the experiment and the mRNA expression of target genes was analyzed by qPCR.

Example 2

AHR Signaling Pathway in the Ileum of Mice with NEC

Referring now to FIG. 1, the mRNA expression of Cyp1a1, the down-stream gene of aryl hydrocarbon receptor (AHR) signaling, was quantified in the ileum of experimental NEC models. Data are represented as mean±SEM; *p<0.05 between indicated groups; each dot represents an individual mouse. Compared with the vehicle treated mice, abacavir and lansoprazole, but not tranilast nor raberprazole, activated AHR signaling pathway in the ileum of mice with NEC, revealing that abacavir and lansoprazole acts as AHR agonist in vivo.

Example 3

Expression of Proinflammatory Cytokine Tnf in the Ileum of Mice with NEC

Referring now to FIG. 2, the mRNA expression of proinflammatory cytokine tumor necrosis factor alpha (Tnf) was quantified in the ileum of experimental NEC models. Data are represented as mean±SEM; *$p<0.05$ between indicated groups; each dot represents an individual mouse. Tnf expression was significantly induced in vehicle-treated NEC group compared with healthy control group, revealing that the NEC was successfully induced. Administration of abacavir, lansoprazole, or tranilast significantly attenuated Tnf expression compared with vehicle-treated group, revealing that the disease severity was significantly reduced.

Example 4

Expression of Proinflammatory Cytokine IL-6 in the Ileum of Mice with NEC

Referring now to FIG. 3, the mRNA expression of proinflammatory Interleukin-6 (IL-6) was quantified in the ileum of experimental NEC models. Data are represented as mean±SEM; *$p<0.05$ between indicated groups; each dot represents an individual mouse. IL-6 expression was significantly induced in vehicle-treated NEC group compared with healthy control group, revealing that the NEC was successfully induced. Administration of abacavir, lansoprazole, or tranilast significantly attenuated IL-6 expression compared with vehicle-treated group, revealing that the disease severity was significantly reduced.

Example 5

Expression of NEC Marker S100a8 in the Ileum of Mice with NEC

Referring now to FIG. 4, the mRNA expression of NEC marker S100 calcium binding protein A8 (S100a8) was quantified in the ileum of experimental NEC models. Data are represented as mean±SEM; *$p<0.05$ between indicated groups; each dot represents an individual mouse. S100a8 expression was significantly induced in vehicle-treated NEC group compared with healthy control group, revealing that the NEC was successfully induced. Administration of abacavir, lansoprazole, tranilast, or raberprazole significantly attenuated S100a8 expression compared with vehicle-treated group, revealing that the disease severity was significantly reduced.

Example 6

Expression of NEC Marker Lcn2 in the Ileum of Mice with NEC

Referring now to FIG. 5, the mRNA expression of NEC marker lipocalin 2 (Lcn2) was quantified in the ileum of experimental NEC models. Data are represented as mean±SEM; *$p<0.05$ between indicated groups; each dot represents an individual mouse. Lcn2 expression was significantly induced in vehicle-treated NEC group compared with healthy control group, revealing that the NEC was successfully induced. Administration of abacavir, lansoprazole, or tranilast significantly attenuated Lcn2 expression compared with vehicle-treated group, revealing that the disease severity was significantly reduced.

Example 7

Expression of NEC Marker iFabp in the Ileum of Mice with NEC

Referring now to FIG. 6, the mRNA expression of NEC marker intestinal fatty acid-binding protein (iFabp) was quantified in the ileum of experimental NEC models. Data are represented as mean±SEM; *$p<0.05$ between indicated groups; each dot represents an individual mouse. IFabp expression was significantly induced in vehicle-treated NEC group compared with healthy control group, revealing that the NEC was successfully induced. Administration of lansoprazole, tranilast, or raberprazole significantly attenuated iFabp expression compared with vehicle-treated group, revealing that the disease severity was significantly reduced.

Example 8

Maternal Indole-3-Carbinol (I3C) Administration NEC

Experiment Design

All female mice were fed a synthetic diet that does not contain any ligands of aryl hydrocarbon receptor (AHR). The pups whose mums received 25 mg/kg indole-3-carbinol (I3C) by oral gavage starting from the embryonic age 7 (E7) of the fetus until the postnatal day 7 (P7) were included in maternal I3C-rich group, while the pups whose mums received vehicle were included in maternal I3C-free group. Necrotizing enterocolitis (NEC) was induced in 7-day-old mouse pups by gavage feeding and hypoxia exposure for 4 days. The ileum was harvested at the end of experiment and the mRNA expression of target genes was analyzed by qPCR.

AHR Signaling Pathway in the Ileum of Mice with NEC

Referring now to FIG. 7, the mRNA expression of Cyp1a1, the down-stream gene of AHR signaling, was quantified in the ileum of experimental NEC models. Data are represented as mean±SEM; *$p<0.05$ between indicated groups; each dot represents an individual mouse. Maternal administration of I3C to pregnant mums significantly activated the AHR signaling pathway in the ileum of the offspring compared with the pups whose mums received vehicle.

Expression of Proinflammatory Cytokine Tnf in the Ileum of Mice with NEC

Referring now to FIG. 8, the mRNA expression of proinflammatory cytokine tumor necrosis factor alpha (Tnf alpha) was quantified in the ileum of experimental NEC models. Data are represented as mean±SEM; *$p<0.05$ between indicated groups; each dot represents an individual mouse. Tnf alpha expression was significantly induced in NEC group compared with healthy control group, revealing that the NEC was successfully induced. In NEC groups, maternal administration of I3C to pregnant mums significantly reduced the Tnf alpha expression in the ileum of offspring compared with the pups whose mums received vehicle, revealing that the disease severity was significantly reduced by maternal I3C administration.

Expression of Proinflammatory Cytokine IL-6 in the Ileum of Mice with NEC

Referring now to FIG. 9, the mRNA expression of pro-inflammatory cytokine Interleukin-6 (Il6) was quantified in the ileum of experimental NEC models. Data are represented as mean±SEM; $*p<0.05$ between indicated groups; each dot represents an individual mouse. Il6 expression was significantly induced in NEC group compared with healthy control group, revealing that the NEC was successfully induced. In NEC groups, maternal administration of I3C to pregnant mums significantly reduced the Il6 expression in the ileum of offspring compared with the pups whose mums received vehicle, revealing that the disease severity was significantly reduced by maternal I3C administration.

Example 9

I3C Reduces Tlr4 mRNA Expression Via MicroRNAs In Vitro

Rat intestinal epithelial cell line IEC-6 was treated with aryl hydrocarbon receptor (AHR) agonist indole-3-carbinol (I3C) for 4 and 6 hours, and then the expression of Toll-like receptor 4 (Tlr4) mRNA and the microRNAs, which have been reported to down-regulate Tlr4 transcription, were quantified, respectively.

Referring now to FIG. 22, the mRNA expression of Tlr4 was quantified in IEC-6 cells treated with AHR agonist I3C for 6 hours. Data are represented as mean±SEM; $*p<0.05$ between indicated groups; each dot represents an individual sample. Treatment of I3C significantly reduced the expression of Tlr4 mRNA.

Referring now to FIG. 23, the expression of let-7i, miR-223, and miR-146b, which are microRNAs known to inhibit Tlr4 mRNA expression, was quantified in IEC-6 cells treated with AHR agonist I3C for 4 hours. Data are represented as mean±SEM; $*p<0.05$ between indicated groups; each dot represents an individual sample. Treatment of I3C significantly increased the expression of let-7i, miR-223, and miR-146b.

Example 10

I3C Reduces Tlr4 mRNA Expression Via microRNAs In Vivo

Experiment Design

Neonatal mice at the age of 7 days old were given AHR agonist I3C (25 mg/kg) via oral gavage, and the ileal expression of Tlr4 mRNA and microRNAs, which have been reported to down-regulate Tlr4 transcription, were quantified after 24 hours.

Referring now to FIG. 24, the mRNA expression of Tlr4 was quantified in the ileum of neonatal mice treated with AHR agonist I3C. Data are represented as mean±SEM; $*p<0.05$ between indicated groups; each dot represents an individual mouse. Administration of I3C significantly reduced the expression of Tlr4 mRNA in the ileum of neonatal mice.

Referring now to FIG. 25, the expression of let-7I, miR-223, and miR-146b, which are microRNAs known to inhibit Tlr4 mRNA expression, was quantified in the ileum of neonatal mice treated with AHR agonist I3C. Data are represented as mean±SEM; $*p<0.05$ between indicated groups; each dot represents an individual mouse. Administration of I3C significantly increased the expression of let-7i, miRNA-223, and miR-146b in the ileum of neonatal mice.

Example 11

Overview

The presently disclosed subject matter, in part, is directed to understanding what leads to the development of necrotizing enterocolitis (NEC) and to developing novel treatment strategies based upon the discovery that the aryl hydrocarbon receptor (AHR) regulates inflammation in the premature intestine.

NEC is the leading cause of death from gastrointestinal disease in premature infants. This devastating disease affects up to 10% of preterm children, is associated with an overall mortality of up to 50%, and requires an average annual treatment cost of 2-3 billion dollars. The typical patient with NEC is a premature infant who displays the rapid progression from mild feeding intolerance to abdominal distention, systemic sepsis and then death within 24 hours. Half of all patients with NEC will require laparotomy, which typically reveals severe inflammation and patchy intestinal necrosis. It is sobering to note that there is no effective cure for NEC, and the overall survival has not changed in the past 30 years.

Current thinking in the field was summarized by a landmark National Institute of Child Health and Development workshop, and further supported by the recent publication in *Nature Reviews in Gastroenterology and Hepatology*, which concludes that "NEC can be thought to arise from an exuberant inflammatory response to bacterial colonization in the intestine of premature infants." Importantly, the pathways that mediate the heightened pro-inflammatory response of the premature intestinal mucosa to bacterial colonization, and strategies to reverse this pro-inflammatory response, remain incompletely understood.

The presently disclosed subject matter seeks, in part, to investigate and then reverse the pathways by which the premature host mounts an exuberant pro-inflammatory response to bacteria leading to NEC. To do so, the hypothesis that the aryl hydrocarbon receptor (AHR) within the intestinal epithelium serves to restrain the hyper-inflammatory response of the premature intestinal epithelium to bacterial stimuli and that a loss of AHR signaling leads to unrestrained bacterial signaling and the induction of NEC will be tested. Whether strategies that activate AHR signaling, including those administered to the pregnant mother, can offer a novel approach for the prevention and treatment of NEC also will be evaluated.

Preliminary Data

The development of NEC requires TLR4 signaling in the intestinal epithelium. In seeking to understand the biological underpinnings of NEC, it has been discovered that activation within the intestinal epithelium of the receptor for gram-negative bacteria, namely toll-like receptor 4 (TLR4), is critical for the development of NEC. Specifically, it has been shown that the expression of TLR4 in the intestinal epithelium is significantly higher in human infants and mice with NEC as compared with non NEC counterparts (FIG. 10). Further, mice that lack TLR4 in the intestinal epithelium (herein referred to as TLR4$^{\Delta IEC}$ mice) or globally (TLR4$^{-/-}$) were generated and then subjected to the well validated NEC model at 7 days of age. Mice were gavaged with formula, i.e., Similac Advance infant formula (Abbott Nutrition): Esbilac caninice milk replacer (PetAb) in a 2:1 ratio at 50 µL/g every 3 hours, 10 mins hypoxia (5% $O_2$ 95% $N_2$ in a Billups-Rothenberg chamber) twice daily for four days, and oral gavage of bacteria ($1 \times 10^5$ cfu/mL) obtained from the stool of a patient with severe NEC. This experimental protocol induces patchy small intestinal necrosis, intestinal edema, and mucosal disruption very similar to human NEC in wild-type mice (FIG. 10), while mice lacking TLR4 in the intestinal epithelium (TLR4$^{\Delta IEC}$ mice) or globally (TLR4$^{-/-}$) were protected from NEC development. Mechanistically, TLR4 activation in the intestinal epithelium leads to an increase in apoptosis and a reduction in proliferation within the intestinal epithelium which leads to mucosal injury (FIG. 11). The subsequent translocation of bacteria into the mesenteric circulation activates TLR4 on the endothelial lining leading to reduced eNOS, mesenteric vasoconstriction and the intestinal ischemia that characterizes NEC. Importantly, TLR4 expression is higher in the premature intestine as compared with the full-term intestine and rises during gut development, reflecting its role in normal intestinal cell fate specification (FIG. 12). When the baby is born prematurely, the elevated TLR4 expression in the intestine is then activated by colonizing microbes in the lumen of the gut, switching TLR4 from a developmental to a pro-inflammatory role, leading to NEC. The presently disclosed subject matter seeks to develop novel preventive and treatment strategies for NEC based in part upon the recently identified role for the ability of the Aryl Hydrocarbon Receptor (AHR) to restrain TLR4 signaling within the intestinal epithelium of the premature host.

Signaling via the Aryl Hydrocarbon Receptor (AHR) in the intestinal epithelium protects against the development of necrotizing enterocolitis in newborn mice (FIG. 13). The Aryl Hydrocarbon Receptor (AHR) is a transcription factor which is activated by dietary ligands, including the specific ligand indole-3-carbinole (I3C) present in crustaceous vegetables, and induces the differentiation of lymphocytes and innate lymphoid cells. AHR is expressed on the intestinal epithelium, and that its expression is reduced in the prenatal bowel compared with postnatal bowel in both mouse and human (FIG. 13). Further, AHR was significantly decreased in mice and humans with NEC, suggesting that a lack of AHR signaling may contribute to NEC (FIG. 13). In support of this possibility, mice lacking AHR globally (AHR$^{-/-}$) or within the intestinal epithelium (AHR$^{\Delta IEC}$) or leukocytes (AHR$^{\Delta Leuk}$ mice) were generated and it was determined that NEC in AHR$^{-/-}$ mice and AHR$^{\Delta IEC}$ mice was significantly more severe than wild-type mice, while NEC in AHR$^{\Delta Leuk}$ mice was as severe as in wild-type mice, as determined by cytokine induction, mucosal injury and blinded severity score according to a published scale.

These data indicate that AHR signaling on the intestinal epithelium as opposed to leukocytes plays a key role in NEC protection. Further, administration of the AHR ligand I3C (oral, 50 mg/kg/day) to wild-type mice but not AHR$^{-/-}$ mice reduced NEC severity as compared with mice fed a standard formula, indicating the benefit of this approach and the specificity of I3C for AHR activation. The presently disclosed subject matter, in part, investigates the role of intestinal AHR loss in the pathogenesis of NEC, and will test whether AHR ligation, including the use of a novel AHR ligand, can prevent NEC.

AHR activation by I3C or breast milk limits TLR4 signaling in the intestinal epithelium (FIG. 14). In seeking to investigate how AHR signaling attenuates NEC severity, whether AHR activation could limit the degree of TLR4 signaling in the gut was investigated. To do so, enteroids were derived from wild-type mice, which are intestinal cultures containing all cell lineages derived from intestinal crypts, as have been described. AHR activation with I3C (200 µM) significantly induced the downstream molecule Cyp1a1 (Cytochrome P450, family-1), and reduced TLR4 signaling induced conditioned media from NEC stool bacteria (1×10$^5$ cfu/mL) as revealed by reduced cytokine induction. AHR activation in mice in response to I3C (50 mg/kg) also induced Cyp1a1 expression (FIG. 14) and reduced TLR4-induced (LPS 5 mg/kg) cytokine induction in the intestinal mucosa in wild type mice (FIG. 14), while AHR$^{\Delta IEC}$ and AHR$^{-/-}$ mice show increased TLR4 expression and signaling (FIG. 14) compared with wild-type mice in response to LPS (5 mg/kg). Within the intestinal mucosa, AHR activation with I3C reversed the deleterious effects of TLR4 activation on enterocyte apoptosis (FIG. 14), and improved mucosal healing.

Breast milk is the most important agent capable of protecting against NEC in humans, which has been shown to act in part via inhibition of TLR4 signaling in mice. In FIG. 15, it is shown that breast milk activates AHR, as revealed by induction of Cyp1, in mice and enteroids, indicating that breast milk contains AHR ligands.

Strikingly, breast milk reduced LPS-induced cytokine induction and NFkB activation (FIG. 15), and reversed LPS-induced apoptosis and restored proliferation in wild-type, but not AHR deficient mice (LPS 5 mg/kg) or cells (FIG. 15). These findings indicate that breast milk inhibits TLR4 signaling via AHR activation. A goal of the presently disclosed subject matter is to understand how AHR signaling by dietary ligands, including those in breast milk, prevents NEC via effects on reduction of TLR4 signaling.

The administration of the AHR ligand I3C to the pregnant mother prevents NEC in the newborn mouse (FIG. 16). Having shown that AHR activation in mice with I3C or breast milk reduces NEC severity, the novel strategy of administration of the AHR ligand I3C to the pregnant mother to prevent NEC in the offspring was investigated. As shown in FIG. 16, the administration of I3C (oral, 50 mg/kg/day) on each day of pregnancy induced the downstream gene Cyp1a1 in the pup intestine, confirming that AHR activation in the developing mouse intestine could be achieved in utero. Strikingly, treatment of pregnant mice with I3C (50 mg/kg/d) significantly reduced NEC severity in the pup, as manifested by reduced cytokine induction, mucosal injury and apoptosis and improved proliferation (FIG. 16). Another aspect of the presently disclosed subject matter is to develop a diet rich in AHR ligands that could be administered to the mother, and protect against the development of NEC.

Discovery of a Novel AHR Ligand, "A18", Whose Oral Administration Prevents NEC in Mice, and Activates AHR and Reduces TLR4 Signaling in Human Tissue Ex Vivo. Another aspect of the presently disclosed subject matter was to identify novel agonists of AHR which could be orally administered to prevent or treat experimental NEC, and which have greater potency and pharmacokinetic properties than the dietary-derived ligand I3C. To do so, an AHR-luciferase screen in intestinal epithelial cells (IEC-6 cells) was developed, then compound libraries were screened, and validation in vitro and in vivo using readouts of AHR activation by measuring the expression of Cyp1 was performed. The lead compound, shown in FIG. 17 is a 369 KDa molecule with the formula $C_{16}H_{14}F_3N_3O_2S$, herein referred to as "A18", attenuated NEC severity when administered orally (300 mg/kg/day) to 7 d old mice, reduced pro-inflammatory cytokine induction and reduced apoptosis, and increased proliferation in mice (FIG. 17). Strikingly, A18 (10 µM) significantly reduced TLR4 signaling (LPS 25 µg/mL) and induced Cyp1a1 expression in human intestine obtained from humans undergoing surgery for NEC (FIG.

17), suggesting a potentially physiologically relevant role for this new compound. The presently disclosed subject matter, in part, explores the efficacy of the AHR agonist, A18, and its analogues, to prevent or treat NEC in mouse and piglet models.

Without wishing to be bound to any one particular theory, based upon the above preliminary results, it is thought that the Aryl Hydrocarbon Receptor (AHR) in the intestinal epithelium plays a previously unrecognized role in restraining the hyper-inflammatory response of the newborn intestinal mucosa to colonizing microbes by limiting the degree of intestinal epithelial TLR4 signaling, thus protecting against NEC, and that activation of AHR by dietary factors, including those in breast milk, can restrain TLR4 signaling and prevent NEC. Further, it is thought that the administration of an AHR ligand to the pregnant mother can reduce NEC severity in the offspring. Finally, it is thought that A18, or its analogues, will represent a novel and effective strategy for NEC prevention and treatment.

Study Design

This first set of studies is designed to develop an agent that could be administered to the mother during pregnancy, which could then protect her neonate against the development of NEC, based upon its activation of the aryl hydrocarbon receptor. Further, this is the first set of studies to investigate the protective properties of breast milk as a consequence of their ability to activate AHR. Perhaps most significantly, a novel AHR ligand ($C_{16}H_{14}F_3N_3O_2S$, i.e. "A18") has been identified which prevents NEC in mice. Backscatter ultrasound-guided microinjection will be used to deliver AHR activators and inhibitors into the lumen of the fetal intestine, which will allow how AHR and TLR4 interact within the premature intestinal epithelium to induce NEC to be precisely defined, and novel transgenic AHR mouse strains that have been developed to be assessed. These experiments therefore have the potential to directly challenge key concepts in NEC research by showing that the unique susceptibility of the premature infant to the development of NEC occurs not solely through non-specific impairment in host immunity or barrier function, but rather through dysregulated effects of AHR resulting in exaggerated TLR4 signaling within the intestinal mucosa leading to a hyper-inflammatory state in response to colonizing microbes.

Approach

Rigor and Reproducibility in the Current Scientific Approach:

Care is always taken to ensure mouse experiments are performed at the same age between groups. Although an effect of gender has not been observed, gender will be randomized in all cases. Studies performed in any cultured cell line (i.e., IEC-6 cells) will be used only between passages 12-15 to ensure that no spontaneous gene alteration occurs, and all mouse genotypes will be confirmed by RT-PCR prior to experimentation.

To Understand the Role of the Aryl Hydrocarbon Receptor in the Newborn Intestinal Epithelium in the Pathogenesis and Treatment of NEC.

A major unresolved question in the field is, "what predisposes a premature infant to the development of NEC in the first place?" In preliminary data, it is shown that the small intestine of humans and mice with NEC is characterized by increased TLR4 (FIG. 10) and reduced AHR expression (FIG. 13), that TLR4 activation by colonizing bacteria leads to mucosal apoptosis and reduced repair (FIG. 10), while treatment of mice with the AHR ligand I3C reduces TLR4 signaling and limits NEC severity (FIG. 13). It is further shown that breast milk, which has long been known to protect against NEC, activates AHR and attenuates TLR4 signaling in vitro and in vivo (FIG. 15). Based upon these findings, the hypothesis that NEC susceptibility is derived from a loss of AHR signaling in the intestinal epithelium leading to the unrestrained effects of pro-inflammatory TLR4 signaling, while activation of AHR by dietary ligands, including those within breast milk, counter TLR4 signaling to prevent NEC will be tested.

Figure 18E:
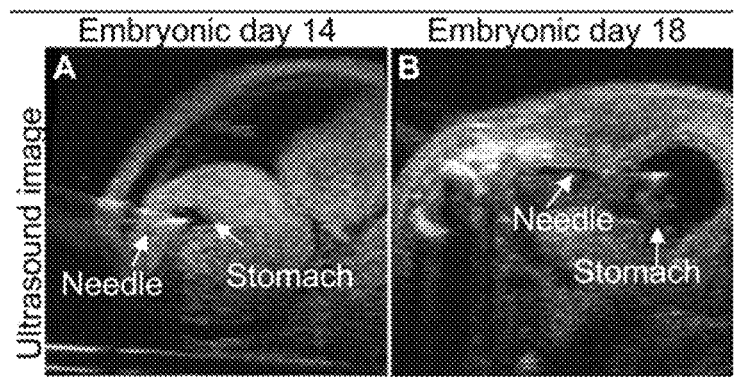
Figure 18E:
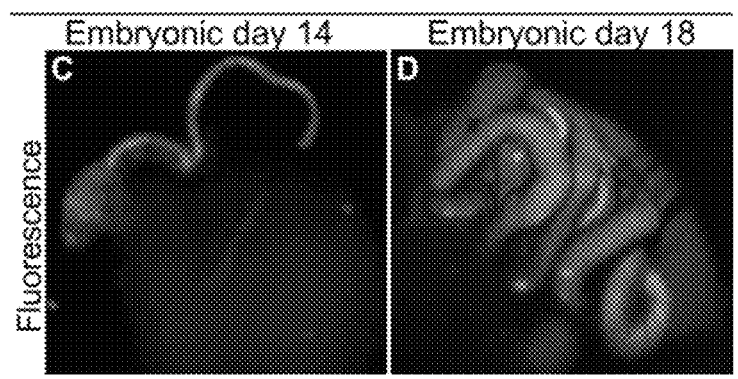
Figure 18E:
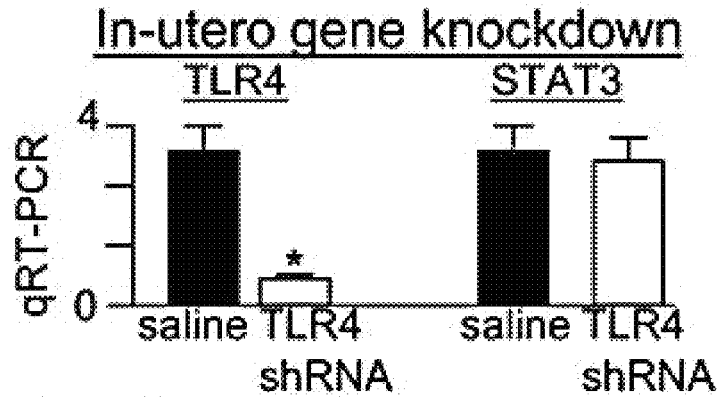

To Explore Whether a Loss of AHR Signaling in the Premature Intestinal Epithelium Leads to Unrestrained TLR4 Signaling and the Induction of NEC.

i. In utero injection of AHR ligands and inhibitors: Whether the susceptibility to NEC is derived from the low AHR expression in the intestinal epithelium of the premature infant, and whether this leads to exaggerated TLR4 signaling will be tested. To do so, the expression of AHR in the fetal intestine will be either increased or decreased, and then the subsequent effects on TLR4 signaling and NEC development will be assessed. A novel backscatter ultrasound microinjection system, which allows for the survivable in utero delivery of AHR activators (I3C, 25 µg) and inhibitors (lentiviral shRNA) directly into the lumen of the fetal mouse intestine will be used (FIG. 18). In parallel, LPS (0.5-2.5 µg) or cultured bacteria from the stool of a patient with severe NEC ($1 \times 10^5$ cfu/mL) will be delivered to activate TLR4, or TLR4 shRNA to knock-down TLR4 expression in the fetal gut as in FIG. 18. Full details of the in utero injection system are provided in recent publications. In brief, time-dated pregnant mice are anesthetized, the uterus is exposed by laparotomy, and a fenestrated dish is placed over the uterus. A single embryo (one uterine saccule) is brought through the fenestration. The ultrasound microscope probe is used to guide the injection apparatus and the indicated reagent is injected directly into the fetal stomach, via a 30 µm glass syringe using a Vevo Imaging Station (VisualSonics). Survival to term is over 80%. Studies will first be performed in wild-type mice or in our $AHR^{-/-}$ or $AHR^{\Delta IEC}$ strains, as well as in the TLR4-NFkB-luciferase strain as published. AHR will be activated in the fetal intestine in utero using injection of I3C (25 µg/dose) or its active metabolite (diindolylmethane, 25 µg/dose), and AHR will be inhibited using lentiviral shRNA which achieves over 80% knockdown in cells. Controls will be injected with saline. The mice will be allowed to deliver to term, and AHR expression and activation will be measured via Cyp1a1 expression by RT-PCR in the intestinal epithelium as in FIG. 13 at 7 days of age, the time at which the NEC model is most effective, and a time which correlates with approximately 34 week infant gut development. TLR4 expression and signaling also will be measured in the intestinal epithelium as in FIGS. 10, 11, and 12 by measuring LPS (5 mg/kg, 6 hours)-induced expression of IL-6, and effects on apoptosis and proliferation as in FIG. 11 after birth (day 7), as well as on day 0 in cases in which LPS (2.5 µg) has been injected in utero. It is anticipated that TLR4 signaling will be increased in mice that were administered AHR shRNA, as manifested by increased IL-6 expression by RT-PCR and increased apoptosis as in FIGS. 10 and 11, and reduced in wild-type mice receiving AHR ligand I3C. In control experiments, it is anticipated that the $AHR^{-/-}$ or $AHR^{\Delta IEC}$ strains will show no effect after I3C injection, but will show exaggerated TLR4 signaling compared with wild type strains.

Having assessed the link between low AHR expression and high TLR4 signaling in the newborn intestine, the effects of inhibition or activation of AHR in utero on NEC development will be assessed. To do so, wild-type or AHR$^{-/-}$ or AHR$^{\Delta IEC}$ mice will be injected with AHR activators or inhibitors as above, then the pups will be separated from the mothers at day 7 and mice will be subjected to the model of hypoxia/formula feed/stool gavage as in FIG. 10, and the degree of mucosal injury, enterocyte proliferation, repair and Cyp1a1 (as a measure of AHR activation) in FIGS. 10 and 11 will be assessed. It is anticipated that inhibition of AHR will lead to increased TLR4 signaling and thus increased NEC severity, demonstrating that AHR plays a restraining role on TLR4 and that its absence leads to an increased predisposition to NEC. In controls, the fetal intestine will be injected in utero with LPS (2.5 µg), and NEC severity will be expected to be increased where in utero TLR4 signaling is increased by LPS, and reduced where AHR signaling is increased by I3C.

The relevance of these studies to the clinical situation seen in NEC in which colonization of the lumen with bacteria occurs will then be determined. To do so, the lumen of the mouse will be injected in utero with bacteria or with conditioned media from stool from patients with NEC and the degree of additional inflammation that is achieved will be assessed in conditions in which AHR signaling is increased or decreased in utero as above. It is anticipated that intraluminal activation of TLR4 with bacteria or AHR ligands will result in exaggerated proinflammatory signaling and the development of NEC either spontaneously or in the subsequent model.

ii. Evaluation of human control and NEC for of AHR and TLR4 signaling ex vivo: Whether a lack of AHR signaling leads to the development of NEC in humans will be explored next. To do so, intestinal specimens after surgery will be collected for NEC or non-NEC conditions. The expression of TLR4 and AHR in control and NEC tissue will be determined by RT-PCR and it is anticipated that NEC will be associated with reduced AHR and increased TLR4 expression. Then, whether NEC is associated with reduced AHR ability to restrain TLR4 signaling will be assessed and tissues will be treated with the AHR ligand I3C (50 mg/kg) and LPS (5 mg/kg, 6 hours) ex vivo, and the degree of AHR signaling will be assessed by measuring Cyp1a1 expression and TLR4 signaling by expression of TNFα (see signaling in human tissue in FIG. 17). A power analysis indicates that this study will require 15 NEC and control specimens. It is anticipated that human tissue showing reduced expression of AHR will have more pronounced LPS signaling and higher NEC severity, providing human correlation with the mouse studies showing that reduced AHR leads to heightened TLR4 and the predisposition to NEC.

To Understand the Mechanisms by which AHR Activation by Dietary Ligands, Including Those in Breast Milk, Limit Pro-Inflammatory TLR4 Signaling to Prevent Necrotizing Enterocolitis.

In FIG. 15, the surprising observation that administration of breast milk to mice activates AHR and prevents TLR4 signaling was made, raising the possibility that breast milk protects against NEC through the AHR ligands that it contains. The presently disclosed subject matter also seeks to understand the capacity of breast milk to protect against NEC by activating AHR and inhibiting TLR4, and to determine the mechanisms involved.

The general approach will be to treat intestinal epithelial cells (IEC-6 cells and 30 enteroids) or wild type or AHR deficient mice (both AHR$^{\Delta IEC}$ or AHR$^{-/-}$) with either I3C (200 µM for cells and 50 mg/kg for mice), or with breast milk, which will be obtained from pregnant mice that were fed either an I3C-rich or I3C-deficient diet. In FIG. 16, it is shown that feeding the AHR ligand I3C (50 mg/kg) to the pregnant mother yields breast milk that induces greater Cyp1a1 expression—a marker of AHR activation—in the intestinal mucosa of 7 d old pups than breast milk from mothers fed an I3C-deficient diet (FIG. 19). Breast milk will be obtained as described in Mucosal Immunology in which oxytocin [0.15 IU SQ per kg of body weight for 3 minutes prior to milk being collected] is administered to nursing mothers (p8) and 1 mL of breast milk will be obtained per mouse using a customized mouse breast pump. In addition to the enteroids, the mechanisms by which AHR activation with I3C (200 µM) or breast milk limits TLR4 signaling in IEC-6 cells, a well validated enterocyte cell line, which has been shown to express TLR4 and AHR, and which undergo apoptosis, impaired proliferation, cytokine induction and impaired migration in the presence of LPS (1-10 µg/mL×6 h) will be assessed.

Enteroids from human intestine will be obtained from resected tissue from patients with NEC or control patients. IEC-6 cells or mouse/human enteroids will then be treated with LPS (100 µg/mL) and I3C (200 µM) or breast milk, and the expression of TLR4 and the critical TLR4-downstream genes MyD88 and TRIF will be assessed by RT-PCR. Should AHR activation alter the expression MyD88 or TRIF, the experiments will be repeated in enteroids from MyD88 or TRIF KO mice, which is anticipated to show no further protection by I3C activation against LPS signaling. MyD88 or TRIF will be over-expressed using adenoviral-MyD88 or adeno-TRIF genes, which result in high expression in enteroids or IEC-6 cells, on the CMV promoter, and which it is anticipated will reverse the effects of AHR activation by I3C or breast milk, confirming the importance of these pathways. Studies will be repeated in enteroids from AHR deficient mice, and from IEC-6 cells lacking AHR as shown in FIG. 15.

The effects of AHR activation on expression of anti-inflammatory genes known to counteract pro-inflammatory TLR4 signaling will then be studied. These candidate genes are specifically selected from known anti-TLR4 pathways, and it will be determined whether they are activated by AHR, namely Sigirr (Single Ig IL-1 related receptor), in which mutations lead to increased NEC severity and IRAK-m (interleukin-1 receptor associated kinase-m), which have been shown to prevent TLR4 signaling in mice. Sigirr and IRAK-m expression will be measured by RT-PCR in wild type enteroids treated with I3C (200 µM) and breast milk, and the degree of LPS-induced IL-6 expression will be measured by RT-PCR. In control experiments, enteroids from both AHR$^{\Delta IEC}$ or AHR$^{-/-}$ mice will be tested, given that breast milk may have multiple other ligands that could mediate effects, and the interest here is in understanding the effects of breast milk that are due to AHR activation. It is anticipated that AHR activation will upregulate these anti-TLR4 pathways, and explain, in part, the protection of breast milk, via AHR, on TLR4 inhibition.

Based upon the above results, the mechanisms explaining how AHR activation prevents NEC will be assessed. To assess the importance of the downstream TLR4 signaling molecules, NEC will be induced in MyD88 or TRIF deficient mice with I3C (50 mg/kg) or breast milk and whether AHR activation confers additional protection will be assessed. In parallel, studies in the Sigirr KO or the IRAK-m KO mouse will be performed and treated with I3C or breast milk and again whether AHR signaling confers any additional protection will be assessed.

Finally, whether reduced intestinal TLR4 signaling is required for the protection conferred by activation of AHR by breast milk or I3C will be determined. To do so, studies will be performed in the TLR4-$^{villin-over}$ strain, in which TLR4 is over-expressed selectively in the intestinal epithelium on a TLR4$^{-/-}$ background. These mice develop severe NEC, providing additional proof-of-concept that TLR4 in the intestinal epithelium is sufficient to cause this disease. TLR4-$^{villin-over}$ mice will then be subjected to NEC, administered breast milk or I3C (50 mg/kg) by oral gavage, and Cyp1a1 expression will be measured as a readout of AHR activation, and TLR4 signaling by determining IL-6 induction in the intestinal epithelium, which is expected to be very high in the intestines of TLR4-$^{villin-over}$ mice compared with wild-type mice. It is anticipated that while I3C or breast milk will still induce Cyp1a1 expression, there will not be significant protection against NEC, confirming that AHR activation by ligands including those in breast milk act to prevent NEC via inhibition of TLR4 signaling.

Alternative Strategies.

i. Effects on the immune system. The presently disclosed focus on the role of AHR on TLR4 signaling in the gut represents a novel departure from other studies in the field, which have largely focused on the ability of AHR to cause an anti-inflammatory effect through effects on innate lymphoid cells (ILCs). ILCs are not a focus in the present study as no increased NEC severity in the lys-AHR-CKO population has been observed, and that in a recent publication, very few ILCs in mouse or human NEC were measured. However, if it is determined that the effects of AHR activation on the intestinal epithelium are minimal or incomplete, the role of AHR signaling on lymphoid cells will be explored. This will be done by first isolating the ILCs in the presence or absence of I3C in the presence of NEC, in wild-type and AHR transgenic strains.

ii. Efficiency of in utero AHR knockdown. Although >80% knockdown of AHR has been achieved using shRNA, if results of AHR shRNA are partial, a tamoxifen inducible AHR knockdown will be investigated by breeding the villin-ert-cre with the AHR-loxp, and administered hydrotamoxifen (2 mg/mouse), which will achieve AHR knockdown after 48 h.

iii. Other effects of breast milk. Although it is shown that breast milk inhibits TLR4 signaling in part via AHR activation (FIG. 15), potential AHR ligands within breast milk have not yet been thoroughly examined. In preliminary data, it has been shown that human milk oligosaccharides (HMO's) and epidermal growth factor (EGF)—two molecules enriched within breast milk that have been shown to prevent NEC—can activate AHR in mice, leading these molecules to be explored as AHR ligands.

Further, it is recognized that there are other anti TLR4 signaling pathways including those mediated by TLR9, nod2 and siggir, and further analysis of the TLR4 signaling PCR array platform from Biorad, and/or RNA-seq on wild type and breast milk treated TLR4 KO mouse samples, in the Genomics Core, can be performed to identify downstream genes of interest.

To Determine the Effects and Mechanisms by which the Administration of a Diet Rich in AHR Ligands to the Pregnant Mother Protects Against NEC in the Offspring.

Rationale: The surprising observation that the administration of the AHR ligand I3C (50 mg/kg/day) to the pregnant mother from days e12.5 to term leads to expression of Cyp1a1 in the intestinal epithelium of both the mother and the fetus, confirming AHR activation (FIG. 15), and leads to reduced NEC severity in the offspring as revealed by decreased IL-6 expression and improved histology, and reduced enterocyte apoptosis. Based on this preliminary data, the efficacy of intra-partum AHR activation to the pregnant mother to prevent NEC will be investigated.

The window of effectiveness for intra-partum AHR administration for NEC protection will first be determined. To do so, a time- and dose-response will be performed in which the AHR ligand I3C will be oral administered to the pregnant mother from e12.5 until term, at a dose of 5-50 mg/kg/day. Cyp1a1 RT-PCR will be measured in the fetal/pup and maternal intestines, as a readout of AHR activation, and NEC on day 7 will be induced as in FIG. 10, and NEC severity will be evaluated. In control experiments, pregnant mothers will be administered an I3C-deficient diet (obtained from BioServ as in FIG. 15), and I3C will be administered to AHR$^{-/-}$ mothers crossed with AHR$^{-/-}$ fathers, which should show no Cyp1a1 expression and no protection from NEC. It is expected that, in wildtype mice, there will be a time and dose dependence on the strength at which I3C administration will protect against the development of NEC.

Next, whether either maternal or fetal AHR signaling is required for NEC protection will be investigated (seen in FIG. 13 and investigated above), and studies will be performed in AHR$^{+/-}$ mothers who were bred with AHR$^{+/-}$ males, so that the fetuses will either by AHR$^{+/+}$ or AHR$^{+/-}$ or AHR$^{-/-}$. Pregnant mice will be administered an I3C-rich or I3C-deficient diet as above, and the degree of protection will be compared with the genotype of the offspring, blinded to the genotype until after the analysis. It is expected that the AHR-deficient mice will show more severe NEC and no benefit from maternal I3C, indicating that the effect of I3C is achieved through delivery to the fetus, as opposed to modulation of the maternal environment. By contrast, if similar protection is observed in the AHR$^{-/-}$ pups, this will suggest that the effects are indeed maternal in origin, and in that case the effects of I3C on maternal immune responses will be investigated in detail, by first performing studies in pregnant mice lacking AHR on the leukocytes (lys).

Finally, whether the AHR ligand I3C that was delivered in pregnancy to the mother could cross into the breast milk and confer benefits in the postnatal period will be evaluated. To do so, pups will be cross-fostered with a mother who had been administered I3C (50 mg/kg) or saline throughout pregnancy, with either wild-type or AHR$^{\Delta IEC}$ pups, and the mother will be maintained on an I3C-rich or I3C-deficient diet. The fostering will be allowed to occur for 3 to 9 days, and then NEC will be induced as in FIG. 10 and the effects on NEC severity will be measured. In parallel, breast milk will be obtained from the mothers who had received either saline, I3C-deficient or I3C-enriched diet, and the "spiked" milk will be administered to mice to determine whether greater NEC protection can be achieved as compared with those receiving standard breast milk. This is important as up to 10% of NEC occurs in breast fed infants, so augmentation of breast milk may have clinical relevance to these patients.

Assessment of the Role of AHR Activation in the "Stressed" Mother on NEC Prevention.

Rationale: Having determined the effects of intra-partum I3C administration on the fetus during gestation, these findings will be extended toward the clinical situation of a "stressed" mother using a well validated model of sepsis in pregnancy.

Two approaches will be undertaken to induce a stressed state in the mother. In the first, the technique of Aisenberg et al will be adopted and serial injections of low-dose LPS (0.26 mg/kg on day e15.5 then 0.52 mg/kg on day e16.5) or saline will be performed into the pregnant mouse to induce a hyper-inflammatory state consistent with that seen in the setting of preterm birth. This approach typically results in premature birth in the mouse with a mean delivery at e17.5 days. In all cases, either I3C-rich or I3C-deficient diet will be administered to the pregnant mother, and both wild-type and AHR$^{\Delta IEC}$ pups will be collected after birth and induced to develop NEC according to FIG. 10. It is expected that NEC will be more severe after LPS injection, and that I3C administration will reduce NEC severity in wild type, but not AHR$^{\Delta IEC}$ pups.

In the second approach, a focused inflammatory state will be induced in the uterus. Here, timed pregnant wild-type mice, will undergo laparotomy at E17 and be injected with either 25 µg LPS (from *E. coli* 055:B5; Sigma Aldrich, St Louis, Mo.) in 100 µL PBS or 100 µL of PBS inside the uterine muscle between the first and second sac of right horn of murine uterus (FIG. 20). This approach leads to significant uterine inflammation, and differs from the back-scatter intra-intestinal microinjection approach described in hereinabove for its ability to induce marked uterine inflammation. Comparisons between un-injected and injected uterine horns will be achieved by co-injection with India ink to identify injected pups. The pups deliver 1-2 days later in this model. In all cases, I3C-rich or I3C-deficient diet will be administered to the mother, and then NEC will be induced at day 7 in the offspring as in FIG. 10. Control experiments will be performed in pregnant or AHR$^{-/-}$, and TLR4$^{-/-}$. Cyp1a1 expression will be measured in the fetal gut as a marker of AHR activation, and TLR4 signaling and NEC severity as in FIG. 10. It is expected that in wild-type mothers, the "stressed" pups will yield more severe NEC than those that are not stressed, and that I3C administration during pregnancy will reduce TLR4 signaling and NEC severity, confirming the role of maternal AHR signaling in the protection against NEC development.

Alternative Strategies:

1. Toxicity and specificity of I3C—Although unlikely, if maternal toxicity of I3C administration is encountered, the dose of I3C will be reduced accordingly.

2. Effect on fetal gut development—given the finding that TLR4 plays a role in normal gut development, strategies that modulate TLR4 signaling via AHR activation in the developing mouse may adversely affect the crypt-villus axis. If effects are observed after monitoring differentiation of the intestinal epithelium after I3C administration, Notch and Wnt gene expression will be examined to understand the link between AHR and the gut differentiation cascades.

To Evaluate the Role of a Recently Discovered AHR Agonist, A18, in the Prevention and Treatment of NEC in Mice and Piglets.

Rationale: A goal of the presently disclosed subject matter is to develop novel approaches for the prevention and treatment of NEC. The findings in FIGS. 13, 14, and 15 suggest that the identification of novel AHR ligands with high specificity and efficacy could allow this goal to be achieved. Multiple small molecule libraries in AHR-luciferase expressing IEC-6 enterocytes have been screened and a novel class of small molecule AHR agonists have been identified (FIG. 17). A lead compound has the molecular formula $C_{16}H_{14}F_3N_3O_2S$, herein called "A18", which activated AHR in enterocytes in vitro and in vivo, reduced TLR4 signaling and reduced NEC severity in mice (FIG. 17). Significantly, A18 treatment of human tissue obtained at the time of surgical resection for NEC significantly reduced LPS-induced cytokine induction (FIG. 17), raising the possibility of clinical efficacy of A18 via TLR4 inhibition. It is thought that A18 and/or its novel analogs may serve as novel preventive or therapeutic agents for NEC via TLR4 reduction.

Evaluation of the Safety and Efficacy Profile of a Novel Class of AHR Agonists for the Prevention or Treatment of NEC Via Effects on Reduced TLR4 Signaling in the Intestinal Epithelium.

Accordingly, a dose-response for A18 as an anti-inflammatory agent will be developed and then a safety profile will be evaluated based upon its mean effective dose in mice. The readout will be Cyp1a1 activation and reduced LPS-induced TLR4 signaling in the intestine, which will be assessed in vivo by injecting transgenic mice that express NFkB on the luciferase promoter (NFkB-luc mice) with LPS (1 mg/kg) along with luciferin, such that luciferase emission provides a readout of TLR4-NFkB signaling. Escalating doses of A18 (from 1 to 1000 mg/kg) will be used and Cyp1a1 PCR will be measured as a marker of AHR activation. To establish a safety profile for A18 in mice, escalating doses of A18 around the mean effective dose identified above will be used and tissue for evaluation of standard cardiac, neuronal, hematologic and renal parameters in wild-type mice, as well as AHR$^{-/-}$ mice will be obtained to assess off-target effects. This dose will then be used to establish the mean effective dose of A18 in preventing experimental NEC in mice by administration of A18 at 6 h, 1 d or 2 d prior to the onset of NEC, and then assess TLR4 expression, Cyp1a1 expression, and LPS induced IL-6 upregulation in the gut as in FIG. 14 and NEC severity as in FIGS. 13 and 16. To evaluate whether the effects of A18 on reducing NEC severity occur via reduction of TLR4 signaling, studies will be repeated in TLR4-$^{villin-over}$ mice, which express TLR4 on the intestinal epithelium on a TLR4$^{-/-}$ background, and LPS (5 mg/kg, 6 hours) also be administered, and whether the protection of A18 is lost will be assessed. Having shown that administration of A18 can prevent NEC (FIG. 17), whether A18 can treat established NEC in mice will be investigated. To do so, wild-type mice will be subjected to NEC for 1, 2 or 3 days, give A18 at the dose determined above for an additional 1, 2 or 3 days, and NEC severity and TLR4 signaling within the gut will be assessed. It is expected that these studies will reveal that A18 can both prevent and treat experimental NEC and determine the appropriate dose required.

Design, Synthesis and Determination of Structure-Activity Relationships (SAR) of Novel Analogues of A18.

Analogs of A18 will be synthesized, a process that reveals more potent and/or selective derivatives through rational modifications of its primary structure. Chemical modifications of A18 will provide opportunities to remove off-target effects that could narrow the safety profile of this treatment. Given that A18 is structurally expected to modulate cation exchange across the cell membrane, H$^+$/K$^+$ ATPase assays will be an important counterscreen for new compounds. An overview for A18 analog preparation is shown in FIG. 21. Four zones in A18 can be systematically modified (Panel A), 4 to 5 modifications can be introduced at each of the zones and substituents, and sequences, as well as the configuration at the sulfoxide stereocenter, can be varied with the ultimate goal to generate 40-60 close structural congeners of A18 and to determine the corresponding biological data in H$^+$/K$^+$ ATPase and NFkB luciferase screens followed by the studies in experimental NEC to determine structure-activity profile. Panel B in FIG. 21 shows the substitutions contemplated for each of the Zones 1-4 that will be accompanied by target molecular modeling to prioritize designs.

As a representative example, a modular synthesis of analog 7 is shown in Panel C. Pyridine 1 will be oxidized and nitrated to give 2, which is subjected to a nucleophilic aromatic substitution with trifluoroethanol, O-methylated, and α-hydroxymethylated with ammonium persulfate in methanol to provide 3. After conversion to the chloride, substitution with thiol 5 gives thioether 6, which will be assayed in the biological screens, but also subjected to an enantioselective Kagan oxidation to give as an additional analog the sulfoxide 7, a close congener of A18. The metabolic profile of A18 and each analog will be benchmarked via liver microsome cytochrome P450 metabolism studies, and the major metabolite(s) will be determined by LC/HRMS (Liquid Chromatography High Resolution Mass Spectrometry). After demonstrating safety and efficacy within a range of doses (0.1-10 mg/kg), these novel analogs will be utilized in experimental NEC in mice, and assess intestinal inflammation, TLR4 expression, Cyp1a1 expression, Treg upregulation, in the newborn intestinal epithelium. It is expected that novel A18 analogues with superior pharmacokinetic parameters and efficacy than the original compound will be identified.

Based on the findings of FIG. 16, whether administration of A18 can be administered intra-partum and prevent NEC in the offspring will be determined. To do so, A18 on e14.5 to 19.5 at the dose determined above will be administered via oral route in wild type or AHR$^{-/-}$ mice, and NEC will be induced on day 7 in the offspring. Control mice will receive saline. It is expected that the intra-partum administration will reduce the severity of NEC in the offspring, extending the practical application of this novel reagent.

Based upon the above findings, whether A18 can cross the placenta will be determined. Blood from the pup will be obtained after intrapartum administration of A18 as above, a calibration curve will be generated for quantification, and UV (ultraviolet), ELS (evaporative light scattering), and TIC (total ion current) detection methods will be used. To determine the concentration of the key components in the blood, the blood will be diluted with 5% formic acid (1:1-1:10), and the solution will be subjected to centrifugation (2500×g) for 20 min at 4° C. to remove any particulate matter. The resultant supernatant and standard solutions for the compounds of interest will be injected onto an HPLC-HRMS equipped with a C18 analytical column (3 μm/10 cm, 3 mm ID) coupled to a high resolution Orbitrap single quad mass spectrometer in alternating positive and negative ion mass detection modes using electrospray ionization, and concentrations of A18 will be assessed in comparison with a standard curve of blood spiked with known concentrations of A18.

Determination of A18 in Preventing or Treating NEC in a Piglet Model.

To provide a bridge to the potential clinical use of A18 or its analogues, a piglet model of NEC has been established. The piglet is the approximate size of a human premature infant (1000-1200 g), and its intestine expresses TLR4 and shares physiologic and structural properties with the premature human. The piglet model involves delivery of premature piglets via cesarean section at 92% gestation by gavaging a mix of formula feeds containing Pepdite Junior (Nutricia), MCT oil, and whey (at 15 mL/kg every 3 hours (120 mL/kg/day) for 4 days which was supplemented with enteric bacteria from an infant with surgical NEC. This model of piglet NEC will be used to evaluate the efficacy of A18 or its analogues in preventing or treating NEC. For NEC prevention in piglets, A18 will be administered for 24 or 48 h prior to NEC induction; for NEC treatment, A18 will be administered at 24, 48 h or 72 h after NEC induction. In all cases, piglets will be orally gavaged once daily (1 mg/kg/day); saline will be administered to control piglets. The effects on TLR4 expression in the intestine will be evaluated as in FIG. 10 and FIG. 13, and the intestine will be treated ex vivo with LPS in the presence of A18 to determine efficacy as in FIG. 17, and then whether the change in TLR4 signaling or expression accompany the effects on NEC severity will be determined. To define whether a reduction in TLR4 signaling is required for the protection from NEC, LPS (1-10 mg/kg) or bacteria (1×10$^5$ cfu/mL×10 mL) will be administered to the piglets then NEC will be induced and it will be determined whether TLR4 activation can reverse the protection of A18. It is expected that these studies will reveal that A18 or its analogues will be effective in prevention and treatment of NEC in piglets, providing an important bridge to potential clinical use of A18 or its analogues.

Alternate Strategies.

If high toxicity is encountered at low doses of A18 (within the effective range) combinations of A18, as well as its analogues, will be used which will allow for the study at lower concentrations and thus reduced toxicity. In mice, it is possible that the prevention studies may require different dose ranges than the treatment studies, which will be determined by varying the dose accordingly.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Patel R M, Kandefer S, Walsh M C, et al. Causes and timing of death in extremely premature infants from 2000 through 2011. N Engl J Med 2015; 372:331-40.

Stey A, Barnert E S, Tseng C H, et al. Outcomes and costs of surgical treatments of necrotizing enterocolitis. Pediatrics 2015; 135:e1190-7.

Nino D F, Sodhi C P, Hackam D J. Necrotizing enterocolitis: new insights into pathogenesis and mechanisms. Nature reviews Gastroenterology & hepatology 2016; 13:590-600.

Neu J, Walker W A. Necrotizing enterocolitis. N Engl J Med 2011; 364:255-64.

Gribar S C, Sodhi C P, Richardson W M, et al. Reciprocal expression and signaling of TLR4 and TLR9 in the pathogenesis and treatment of necrotizing enterocolitis. J Immunol 2009; 182:636-46.

Egan C E, Sodhi C P, Good M, et al. Toll-like receptor 4-mediated lymphocyte influx induces neonatal necrotizing enterocolitis. J Clin Invest 2016; 126:495-508.

Sodhi C P, Neal M D, Siggers R, et al. Intestinal epithelial Toll-like receptor 4 regulates goblet cell development and is required for necrotizing enterocolitis in mice. Gastroenterology 2012; 143:708-18 e1-5.

Gargaro M, Pirro M, Romani R, Zelante T, Fallarino F. Aryl Hydrocarbon Receptor-Dependent Pathways in Immune Regulation. American journal of transplantation: official journal of the American Society of Transplantation and the American Society of Transplant Surgeons 2016; 16:2270-6.

Good M, Sodhi C P, Yamaguchi Y, et al. The human milk oligosaccharide 2'-fucosyllactose attenuates the severity of experimental necrotising enterocolitis by enhancing mesenteric perfusion in the neonatal intestine. The British journal of nutrition 2016; 116:1175-87.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating or preventing or reducing the risk of necrotizing enterocolitis in a subject in need of treatment thereof, the method comprising administering to the subject one or more AhR agonists selected from the group consisting of abacavir, abacavir sulfate, amlexanox, anagrelide hydrochloride, benzocaine (ethyl p-aminobenzoate), bromindione, catharanthine, eseroline, febuxostat, helenien (xantofyl palmitate), hydralazine hydrochloride, indoprofen, ipratropium bromide, menadione sodium bisulfate, nitazoxanide, phenazopyridine, phenazopyridine hydrochloride, primaquine, tranilast (sb 252218), ziprasidone hydrochloride, indole-3-carbinol (I3C), and a compound of formula (I):

(I)

wherein:
  n is an integer selected from the group consisting of 0, 1, and 2;
  A is selected from the group consisting of:

wherein:
  m is an integer selected from the group consisting of 0, 1, 2, 3, and 4;
  p is an integer selected from the group consisting of 0, 1, 2, 3, 4, and 5;
  each $R_1$ is independently selected from the group consisting of H, $C_1$-$C_6$ alkyl, $C_1$-$C_6$ substituted alkyl, alkoxyl, halogen, and —$CF_3$;
  $R_2$ and $R_3$ are each independently selected from the group consisting of H, $C_1$-$C_6$ alkyl, $C_1$-$C_6$ substituted alkyl, aryl, substituted aryl, heteroaryl, and benzyl;
  $X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;
  $X_2$ is selected from the group consisting of —S—, —S(=O)—, —S(=O)$_2$—, and —C(=O)—;
  $X_3$ is selected from the group consisting of —$CH_2$— and —$NR_5$—, wherein $R_5$ is selected from the group consisting of H, $C_1$-$C_6$ alkyl, $C_1$-$C_6$ substituted alkyl, aryl, substituted aryl, heteroaryl, and benzyl;
  $X_4$ is selected from the group consisting of —N— and —$CR_5$—, wherein $R_5$ is selected from the group consisting of H, $C_1$-$C_6$ alkyl, $C_1$-$C_6$ substituted alkyl, alkoxyl, halogen, and —$CF_3$;
  $R_6$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;
  $R_7$ is selected from the group consisting of H, $C_1$-$C_6$ alkyl, $C_1$-$C_6$ substituted alkyl, alkoxyl, halogen, —$CF_3$, aryl, substituted aryl, heteroaryl, and benzyl;
  or pharmaceutically acceptable salts thereof.

2. The method of claim 1, wherein the one or more AhR agonists is a compound of formula (I):

(I)

wherein:
  n is an integer selected from the group consisting of 0, 1, and 2;
  A is selected from the group consisting of:

wherein:
  m is an integer selected from the group consisting of 0, 1, 2, 3, and 4;
  p is an integer selected from the group consisting of 0, 1, 2, 3, 4, and 5;
  each $R_1$ is independently selected from the group consisting of H, $C_1$-$C_6$ alkyl, $C_1$-$C_6$ substituted alkyl, alkoxyl, halogen, and —$CF_3$;
  $R_2$ and $R_3$ are each independently selected from the group consisting of H, $C_1$-$C_6$ alkyl, $C_1$-$C_6$ substituted alkyl, aryl, substituted aryl, heteroaryl, and benzyl;
  $X_1$ is selected from the group consisting of O, S, and $NR_4$, wherein $R_4$ is selected from the group consisting of H, $C_1$-$C_6$ alkyl, $C_1$-$C_6$ substituted alkyl, aryl, substituted aryl, heteroaryl, and benzyl;
  $X_2$ is selected from the group consisting of —S—, —S(=O)—, —S(=O)$_2$—, and —C(=O)—;

X₃ is selected from the group consisting of —CH₂— and —NR₅—, wherein R₅ is selected from the group consisting of H, $C_1$-$C_6$ alkyl, $C_1$-$C_6$ substituted alkyl, aryl, substituted aryl, heteroaryl, and benzyl;

X₄ is selected from the group consisting of —N— and —CR₅—, wherein R₅ is selected from the group consisting of H, $C_1$-$C_6$ alkyl, $C_1$-$C_6$ substituted alkyl, alkoxyl, halogen, and —CF₃;

R₆ is selected from the group consisting of O, S, and NR₄, wherein R₄ is selected from the group consisting of H, $C_1$-$C_6$ alkyl, $C_1$-$C_6$ substituted alkyl, aryl, substituted aryl, heteroaryl, and benzyl;

R₇ is selected from the group consisting of H, $C_1$-$C_6$ alkyl, $C_1$-$C_6$ substituted alkyl, alkoxyl, halogen, —CF₃, aryl, substituted aryl, heteroaryl, and benzyl; or pharmaceutically acceptable salts thereof.

3. The method of claim 1, wherein the subject is a human subject.

4. The method of claim 3, wherein the human subject is an infant.

5. The method of claim 4, wherein the human subject is a premature infant.

6. The method of claim 1, wherein the administration is enteral administration.

7. The method of claim 6, wherein the enteral administration is oral administration or gastric administration.

8. The method of claim 2, wherein the compound of formula (I) is:

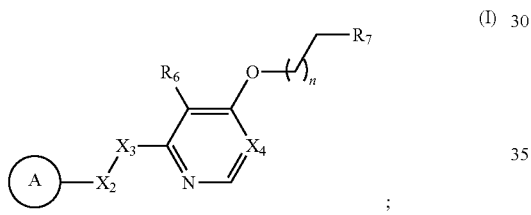

wherein:
n is an integer selected from the group consisting of 0, 1, and 2;
A is:

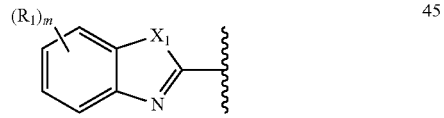

wherein:
m is an integer selected from the group consisting of 0, 1, 2, 3, and 4;

each R₁ is independently selected from the group consisting of H, $C_1$-$C_6$ alkyl, $C_1$-$C_6$ substituted alkyl, alkoxyl, halogen, and —CF₃;

X₁ is selected from the group consisting of O, S, and NR₄, wherein R₄ is selected from the group consisting of H, $C_1$-$C_6$ alkyl, $C_1$-$C_6$ substituted alkyl, aryl, substituted aryl, heteroaryl, and benzyl;

X₂ is selected from the group consisting of —S—, —S(=O)—, —S(=O)₂—, and —C(=O)—;

X₃ is selected from the group consisting of —CH₂— and —NR₅—, wherein R₅ is selected from the group consisting of H, $C_1$-$C_6$ alkyl, $C_1$-$C_6$ substituted alkyl, aryl, substituted aryl, heteroaryl, and benzyl;

X₄ is selected from the group consisting of —N— and —CR₅—, wherein R₅ is selected from the group consisting of H, $C_1$-$C_6$ alkyl, $C_1$-$C_6$ substituted alkyl, alkoxyl, halogen, and —CF₃;

R₆ is selected from the group consisting of O, S, and NR₄, wherein R₄ is selected from the group consisting of H, $C_1$-$C_6$ alkyl, $C_1$-$C_6$ substituted alkyl, aryl, substituted aryl, heteroaryl, and benzyl;

R₇ is selected from the group consisting of H, $C_1$-$C_6$ alkyl, $C_1$-$C_6$ substituted alkyl, alkoxyl, halogen, —CF₃, aryl, substituted aryl, heteroaryl, and benzyl; or pharmaceutically acceptable salts thereof.

9. The method of claim 2, wherein the compound of formula (I) is A18:

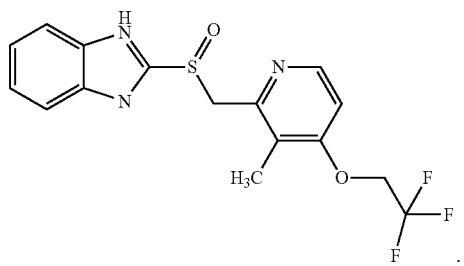

* * * * *

UNITED STATES PATENT AND TRADEMARK OFFICE
CERTIFICATE OF CORRECTION

PATENT NO. : 11,458,141 B2  Page 1 of 1
APPLICATION NO. : 16/617247
DATED : October 4, 2022
INVENTOR(S) : David Hackam et al.

It is certified that error appears in the above-identified patent and that said Letters Patent is hereby corrected as shown below:

In the Claims

Claim 1, Column 45, Lines 50-55 Insert:

-- 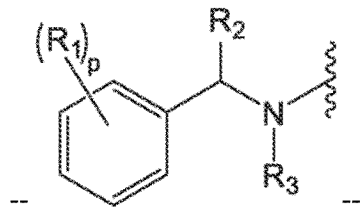 --

Claim 2, Column 46, Lines 45-50 Insert:

-- 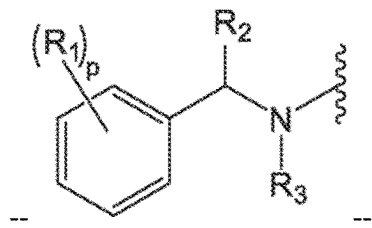 --

Signed and Sealed this
Twenty-fourth Day of January, 2023

Katherine Kelly Vidal
*Director of the United States Patent and Trademark Office*